(12) United States Patent
Viveiros

(10) Patent No.: US 11,406,790 B2
(45) Date of Patent: Aug. 9, 2022

(54) SYSTEM AND METHOD FOR SLEEP ENVIRONMENT MANAGEMENT

(71) Applicant: Walter Viveiros, Brooksville, FL (US)

(72) Inventor: Walter Viveiros, Brooksville, FL (US)

( * ) Notice: Subject to any disclaimer, the term of this patent is extended or adjusted under 35 U.S.C. 154(b) by 48 days.

(21) Appl. No.: 16/946,914

(22) Filed: Jul. 10, 2020

(65) Prior Publication Data

US 2020/0338304 A1    Oct. 29, 2020

Related U.S. Application Data

(63) Continuation-in-part of application No. PCT/US2019/013867, filed on Jan. 16, 2019.
(Continued)

(51) Int. Cl.
*A61M 21/02*      (2006.01)
*G16H 50/30*      (2018.01)
(Continued)

(52) U.S. Cl.
CPC ............ *A61M 21/02* (2013.01); *A61L 9/015* (2013.01); *A61L 9/20* (2013.01); *G16H 50/30* (2018.01);
(Continued)

(58) Field of Classification Search
CPC .......... A61M 21/02; A61M 2021/0016; A61M 2021/0022; A61M 2205/053;
(Continued)

(56) References Cited

U.S. PATENT DOCUMENTS

| 6,585,328 B1 | 7/2003 | Oexman et al. |
| 8,676,662 B1 | 3/2014 | Roberts et al. |

(Continued)

FOREIGN PATENT DOCUMENTS

WO    2016109807 A1    7/2016

OTHER PUBLICATIONS

Rahim, M.N., Hosain, M.K., Islam, M.S., Anjum, M.N., & Rana, M.M. (Mar. 2011). An Electronic Intelligent Hotel Management System For International Marketplace. International Journal of Advanced Computer Science and Applications, vol. 2, No. 3, pp. 93-98. (Year: 2011).*
(Continued)

*Primary Examiner* — Sunita Reddy
(74) *Attorney, Agent, or Firm* — American Patent Agency PC; Daniar Hussain

(57) ABSTRACT

A system and method for sleep environment management is provided. The sleep environment comprises a bed within a sleep space, sleep metric sensors, activity metric sensors, and a sleep environment controller. A server comprises a hardware processor, has access to a database, and comprises a non-transitory, computer-readable storage medium for storing program code, comprising program code to receive at least one sleep metric and at least one activity metric from the sleep environment; record the metrics in the database; analyze the metrics over a period of time to generate a user report and one or more product recommendations; and provide the user report and product recommendations to the sleep environment controller as feedback. Such sleep environment management system and method can improve a user's sleep experience, and allows medical and product presentations to be made to the user.

21 Claims, 20 Drawing Sheets

Related U.S. Application Data

(60) Provisional application No. 62/617,711, filed on Jan. 16, 2018.

(51) Int. Cl.
*A61L 9/20* (2006.01)
*A61L 9/015* (2006.01)
*A61M 21/00* (2006.01)

(52) U.S. Cl.
CPC .......... *A61L 2209/212* (2013.01); *A61M 2021/0016* (2013.01); *A61M 2021/0022* (2013.01); *A61M 2205/053* (2013.01); *A61M 2205/332* (2013.01); *A61M 2205/3368* (2013.01); *A61M 2205/3561* (2013.01); *A61M 2205/502* (2013.01); *A61M 2209/01* (2013.01); *A61M 2230/06* (2013.01); *A61M 2230/62* (2013.01); *A61M 2230/63* (2013.01)

(58) Field of Classification Search
CPC ............ A61M 2205/332; A61M 2205/3368; A61M 2205/3561; A61M 2205/502; A61M 2209/01; A61M 2230/06; A61M 2230/62; A61M 2230/63; A61M 2021/0027; A61M 2021/0044; A61M 2021/0066; A61M 2205/3375; A61M 2205/3553; A61M 2205/3584; A61M 2205/3592; A61M 2205/505; A61M 2205/52; A61M 2205/587; A61M 2205/80; A61M 2230/205; A61M 2230/30; A61M 2230/50; A61L 9/015; A61L 9/20; A61L 2209/212; G16H 50/30; G16H 10/60; G16H 15/00; G16H 20/70; G16H 50/20; A61B 5/021; A61B 5/024; A61B 5/1115; A61B 5/14551; A61B 2560/0242; A61B 5/1116; A61B 5/1118; A61B 5/4815; A61B 5/6889; G06Q 10/06; G06Q 30/0241

USPC ................................................... 600/26–28
See application file for complete search history.

(56) References Cited

U.S. PATENT DOCUMENTS

| | | | |
|---|---|---|---|
| 9,009,898 | B2 | 4/2015 | Morimura et al. |
| 2007/0176920 | A1* | 8/2007 | Raijmakers ............ G09B 5/02 345/418 |
| 2010/0099954 | A1 | 4/2010 | Dickinson et al. |
| 2010/0191551 | A1* | 7/2010 | Drance ................. G06Q 10/02 705/5 |
| 2011/0202396 | A1* | 8/2011 | Viveiros ............... G06Q 30/06 705/14.4 |
| 2011/0230790 | A1* | 9/2011 | Kozlov ................ A61B 5/4812 600/595 |
| 2012/0071706 | A1* | 3/2012 | Martin ................. A61M 21/02 600/27 |
| 2012/0323591 | A1* | 12/2012 | Bechtel ................. G16H 40/20 705/2 |
| 2015/0294086 | A1 | 10/2015 | Kare et al. |
| 2015/0348049 | A1 | 12/2015 | Todasco et al. |
| 2016/0374600 | A1* | 12/2016 | Short .................. A61B 5/7246 434/236 |
| 2017/0020440 | A1 | 1/2017 | Flitsch et al. |
| 2017/0061404 | A1* | 3/2017 | Tunnell ............... G06Q 20/102 |
| 2017/0065792 | A1* | 3/2017 | Bonvallet ............. G16H 50/50 |
| 2017/0192402 | A1 | 7/2017 | Karp et al. |
| 2018/0279946 | A1* | 10/2018 | Nachman .......... A61B 5/02055 |

OTHER PUBLICATIONS

NeuroSpa, "Trial the 'Spa in a Room' Massage chair", Jan. 31, 2018, pp. 1-3.

Lobato et al., "Non-invasive sleep-environment monitoring system", PETRA '15, Jul. 1-3, 2015, Island of Corfu, Greece, 8 pages, published online Jun. 15, 2015, DOI: http://dx.doi.org/10.1145/2769493.2769563.

\* cited by examiner

300

400

800

1800

```
┌─────────────────────────────────────────┐
│                  1810                   │
│  CUSTOM SLEEP SYSTEM PROVIDED TO        │
│  HOSPITALITY PARTNERS                   │
└─────────────────────────────────────────┘
                    │
                    ▼
┌─────────────────────────────────────────┐
│                  1820                   │
│  GUESTS ENJOY THE CUSTOM SLEEP SYSTEM   │
│  EXPERIENCE FIRST-HAND                  │
└─────────────────────────────────────────┘
                    │
                    ▼
┌─────────────────────────────────────────┐
│                  1830                   │
│  GUESTS PURCHASE CUSTOM SLEEP SYSTEMS   │
│  FOR HOME DIRECTLY FROM THE COMPANY-    │
│  MANAGED CUSTOM SLEEP ENVIRONMENT       │
│  BRANDED WEB PORTAL                     │
└─────────────────────────────────────────┘
                    │
                    ▼
┌─────────────────────────────────────────┐
│                  1840                   │
│  SELL-THROUGH DIVIDENDS SHARED WITH     │
│  PARTNERS                               │
└─────────────────────────────────────────┘
```

*FIG. 18*

SYSTEM AND METHOD FOR SLEEP ENVIRONMENT MANAGEMENT

REFERENCE TO RELATED APPLICATIONS

This application is a Continuation-in-Part (CIP) of and claims priority from PCT Application Serial No. PCT/US19/13867, filed on 16 Jan. 2019, entitled "SYSTEM AND METHOD FOR CUSTOMIZED SLEEP ENVIRONMENT MANAGEMENT," which itself claims the benefit of provisional application U.S. Ser. No. 62/617,711, filed on 16 Jan. 2018, entitled "SYSTEM AND METHOD FOR SLEEP ENVIRONMENT MANAGEMENT," the entire disclosures of all of which are hereby incorporated by reference in their entireties herein.

FIELD OF THE INVENTION

The present invention is directed to a system and method for customized sleep environment management. More particularly, the present invention is directed to a system and a method for sleep environment management, comprising Internet of Things (IoT) sensors installed in a sleep environment to be experienced by an end-user, and computing devices for analyzing sleep and activity data to make one or more product recommendations.

BACKGROUND OF THE INVENTION

The statements in this section are provided for context and to help with understanding the invention, and may not constitute prior art.

Quality sleep has increasingly become recognized both in the medical field and in the public arena as playing a critical role in health and well-being. However, the industry standard of mattress and box spring technologies does not fully address issues related to body alignment, pressure relief, temperature control, hygiene, and comfort. Most bedding products still use innersprings of various types or variations on foam, neither of which may provide optimal quality sleep. Further, the bedding industry appears to have historically focused on the mattress rather than the entire sleep environment within a room, where other elements include air quality, temperature, lighting, and noise level are equally important to achieving good quality sleep. The design and management of an optimal sleep environment can help a user better transition to rest, remain in deep sleep, and follow the body's natural circadian rhythm.

The lack of innovation in designs of sleep environments is further coupled with a lack in innovation in presentation, education, and sales to the end-user. Typically, the retail bedding industry universally attempts to sell one of life's most intimate and important products, for example, the bed in our home, without any substantial personal trial or customization whatsoever. Whether in a "warehouse-setting" retail store, or via an Internet-initiated sale shipped to the customer's home, there may be no opportunity to properly test the interaction of this health-critical product with individual and unique bodies. The customization and experimentation of sleep environments are further lacking, with the closest setup being a furniture showroom where customers may view, but not truly experience, a sleep environment immersively.

Thus, there is a need for an improved system and method for sleep environment management that is capable of improving the sleep experience, and integrating sleep-related products and comprehensive information with reference to sleep environment management needs for both end-user individuals and organizations in the supply chain.

It is against this background that the present invention was developed.

BRIEF SUMMARY OF THE INVENTION

Without loss of generality, a brief description of the invention is provided herein.

In one embodiment, provided is a system and method for sleep environment management. The system includes a sleep environment and a server. The sleep environment comprises a bed located inside a walled sleep space; one or more sleep metric sensors for detecting sleep quality of a user; one or more activity metric sensors for human activity recognition within the sleep space, wherein the human activity comprises lying on the bed, sitting, and/or walking; and a sleep environment controller. The server comprises a hardware processor, has access to a database, and comprises a non-transitory, computer-readable storage medium for storing program code, the program code when executed by the processor, causes the processor to receive from the sleep environment, over a period of time, at least one sleep metric of the user from the sleep metric sensors and at least one activity metric of the user from the activity metric sensors; record in the database the at least one sleep metric and the at least one activity metric; analyze the at least one sleep metric and the at least one activity metric over the period of time; generate a user report based on the analysis of the sleep metric and the activity metric; provide feedback to the sleep environment controller based on the user report; analyze the user report for one or more user metric correlations between at least one of the sleep metric and the activity metric, and one or more product parameters of one or more physical products in the sleep environment; generate one or more product recommendations based on the one or more user metric correlations, wherein the one or more product recommendations comprise at least one physical product from the sleep environment; and provide the one or more product recommendations to the user via the sleep environment controller.

In some embodiments, the sleep environment further comprises an air purification unit selected from the group consisting of a hydroxyl generator, a photocatalytic oxidation (PCO) system, an ozone generator, and an ultraviolet (UV) light system. In some embodiments, the sleep environment further comprises at least one of a dynamic lighting system and a dynamic audio system.

In some embodiments, the system further comprises a user device comprising a user interface, and program code to establish a communication channel between the user interface on the user device and the server, wherein the user interface is used by a plurality of stakeholders to access the processor for providing a plurality of product parameters of one or more sleep-related products from the sleep environment, and wherein the server houses the plurality of product parameters of the sleep-related products.

In some embodiments, the system further comprises program code to receive input from the user from a universal remote in the sleep environment; and present information to educate the user with features of sleep-related products presented in the sleep environment on the universal remote.

In some embodiments, the system further comprises program code to correlate the sleep metric and the activity metric from the user across time to predict expected behaviors of the user based on analysis of prior behaviors of the user in similar conditions.

In some embodiments, the system further comprises program code to correlate the sleep metric and the activity metric from two or more users across time to predict expected behaviors of the user based on analysis of prior behaviors of other users in similar conditions.

In some embodiments, the system further comprises program code to provide smart recommendations on sleep-related products for the user based on the correlation of the sleep metric and the activity metric from the two or more users across time.

In some embodiments, the system further comprises program code to provide the user report, subject to user permission, to a hospitality partner for improving the user's hospitality experience.

In some embodiments, the system further comprises program code to provide the user report, subject to user permission, to a hospitality products company for generating customized sleep recommendations and/or product information.

In some embodiments, the system further comprises program code to receive, from the user, user permission to share the user report with a third-party, wherein the third party is selected from the group consisting of a hotel management, a hospitality partner, and a medical professional; and transmit the user report to the third-party, subject to the user permission granted by the user.

In some embodiments, the sleep environment controller adjusts the sleep environment based on the feedback.

In some embodiments, the user report is updated periodically based on new data for the sleep metric and the activity metric.

In some embodiments, the user report identifies a location of the user in the sleep environment.

In some embodiments, the user report identifies a minimum time the user spends in various locations within the sleep environment, and the system further comprises program code to receive data from a sleep sensor in the sleep environment, wherein the data indicates a minimum depression and the minimum time the user spends in the sleep environment.

In some embodiments, the system further comprises program code to detect a location of the user in the sleep environment and continuously record an array of coordinates of the user's location in the user report.

In some embodiments, the system further comprises an actuator for controlling objects within the sleep environment, and further comprises program code to move physical objects within the sleep environment in response to the user's location.

In some embodiments, the system further comprises program code to modify a scent and an air quality within the sleep environment in response to the user's location.

In some embodiments, the system further comprises program code to retrieve stored sleep metrics and activity metrics from the database to generate a population report; and adjust the sleep environment in response to feedback based on the population report.

In some embodiments, the system further comprises program code to receive user-specific feedback from the user; and correlate the user-specific feedback using a series of pre-defined weights and tolerances to collect, interpret, and analyze sleep habits associated with the user.

In some embodiments, the system further comprises an environmental digital logic module integrated into the sleep environment, wherein the environmental digital logic module controls one or more environmental conditions within the sleep environment, the environmental conditions comprising one of temperature and humidity, wherein the environmental digital logic module provides the environmental conditions of the sleep environment to the server for storage in the database along with the sleep metric and the activity metric.

In some embodiments, the sleep metric sensor is selected from the group consisting of a heart rate sensor, an oximeter, a pressure sensor, and a roll-over detector. In some embodiment, the activity metric sensor is selected from the group consisting of a motion sensor and a pressure sensor. In some embodiments, the sleep environment further comprises one of a temperature sensor, a humidity sensor, and an air quality monitor.

In some embodiments, the system further comprises a sound machine for generating a sound selected from the group consisting of a white noise, a sound masking noise, a music, a radio broadcast, an audio reading, and a noise cancellation.

In some embodiments, the system further comprises a voice-enabled interface to the sleep environment controller, wherein the voice-enabled interface comprises a voice-enabled device that is adapted to receive voice commands from the user.

Another embodiment of the present invention is a method for sleep environment management and product recommendations via a hospitality environment, comprising receiving from a sleep environment, over a period of time, at least one sleep metric of a user from one or more sleep metric sensors for detecting sleep quality of the user, and at least one activity metric of the user from one or more activity metric sensors for human activity recognition within the sleep environment, wherein human activity comprises lying on a bed, sitting, and/or walking in the sleep environment; recording in the database the at least one sleep metric and the at least one activity metric; analyzing the at least one sleep metric and the at least one activity metric over the period of time; generating a user report based on the analysis of the sleep metric and the activity metric; providing feedback to the sleep environment controller based on the user report; analyzing the user report for one or more user metric correlations between at least one of the sleep metric and the activity metric, and one or more product parameters of one or more physical products in the sleep environment; generating one or more product recommendations based on the one or more user metric correlations, wherein the one or more product recommendations comprise at least one physical product from the sleep environment; and providing the one or more product recommendations to the user via the sleep environment controller.

Other embodiments of the present invention include an apparatus for sleep environment management, comprising a hardware processor and a non-transitory, computer-readable storage medium for storing program code, the processor having access to a database, and the program code when executed by the processor, which causes the processor to execute the aforementioned steps.

Yet other aspects of the present invention include the methods and processes comprising the steps described herein, and also include the processes and modes of operation of the systems and devices described herein. Other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings. For purposes of clarity, not every component is labelled in every drawing. The drawings are not drawn to scale, with emphasis instead being placed on illustrating various aspects of the techniques and devices described herein.

FIG. 18 shows a schematic of an exemplary sell-through method, according to one embodiment of the present invention.

DETAILED DESCRIPTION OF THE INVENTION

In the following description, for purposes of explanation, numerous specific details are set forth in order to provide a thorough understanding of the invention. It will be apparent, however, to one skilled in the art that the invention can be practiced without these specific details. In other instances, structures, devices, processes, and methods are shown using schematics, use cases, and/or diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Embodiments of the invention as disclosed herein provide an improved system and method for sleep environment management. More particularly, the present invention is directed to providing an improved system and method to properly assess first-hand a user's personal and individual interactions with a sleep environment, including a bed on which they may spend a significant portion of their lives.

Sleep Environment Management System

Figure 1:
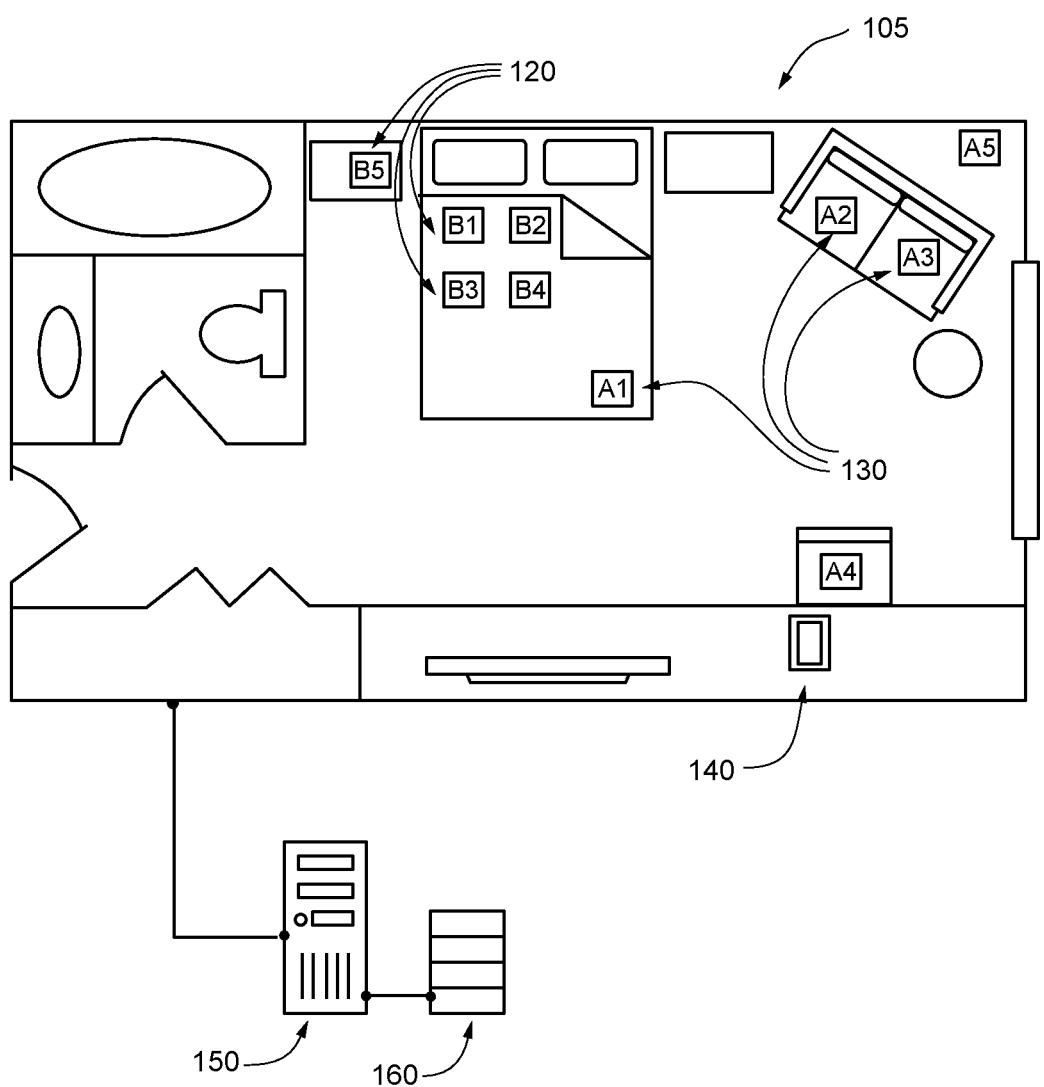
FIG. 1 shows a schematic of an exemplary sleep environment established and managed according to one embodiment of the present invention.

FIG. 1 shows a schematic 100 of an exemplary sleep environment 105 established and managed according to one embodiment of the present invention. In this illustrative example, sleep environment 105 is a bedroom, comprising a bed located inside the walls of the bedroom. To optimize the use of such a sleep environment in helping a user prepare, transition and remain in deep sleep, an analytical approach based on a feedback cycle may be employed to adjust bed incline, air quality, temperature, lighting, noise, and other elements of sleep environment 105.

More specifically, one or more sleep metric sensors 120 including B1, B2, B3, B4, and B5 may be installed on or near the bed to detect one or more sleep metrics for determining a sleep quality of a user resting or sleeping on the bed. In some embodiments, such sleep metric sensors may be placed above, inside, or under the mattress, on the night stand, above or on the head or foot of the bed, or in other proximate locations around the bed. In various embodiments, any data collection device, sensor, or module that detects and measures physical characteristics of the user may be used as a sleep metric sensor, even if data collection occurs while the user is awake instead of asleep. For example, in some embodiments, such sleep metric sensors may include pressure sensors spread throughout the mattress area for detecting the position, spinal alignment, and body conformation of the user while the user lies in bed. In some embodiments, such pressure sensors may be combined with an embedded gyroscope or a wearable device to detect roll-over movements during sleep. Roll-over frequency is indicative of light and deep sleep stages. In some embodiments, such sleep metric sensors may include body temperature sensors such as a thermal imaging camera that can estimate body temperature non-intrusively. Body temperature also fluctuates throughout the day; getting cooler helps one fall and stay asleep, while body temperature rises towards the morning in preparation for wakefulness. In some embodiments, respiratory rate, oxygen saturation, and/or heart rate of the user may be monitored using a wearable pulse oximeter.

Moreover, one or more activity metric sensors 130 including A1, A2, A3, A4, and A5 may be installed throughout the sleep space, for detecting or recognizing human activities within the sleep space. It is established that in addition to time and duration of sleep, activities leading up to sleep often affect sleep quality. For example, relaxing activities such as reading and yoga in bed often allow the body and mind to slow down, whereas blue light from electronics such as a smartphone or a tablet can throw one off the circadian rhythm, making falling asleep more difficult. Any data collection device, sensor, or module that detects and measures user activity within the sleep space may be viewed as an activity metric sensor. For example, the activity metric sensor may be a motion sensor or a pressure sensor. User activity may include lying down, sitting, standing still, walking, reading, typing, watching TV, using a mobile computing device, and so forth. In some embodiments, user activities may be categorized relative to objects within the sleeping space. For example, user activities may be further classified into lying down on the bed, lying down on a sofa, sitting on the bed, sitting on the soft, sitting in a chair, standing near a door, standing near a window, reading in bed, and typing on the sofa. In some embodiments, different human activities may occur concurrently. For example, the user may lie in bed and read, lie in bed and stretch, sit on the sofa and watch TV, etc.

In some embodiments, a single physical sensor may serve as both a sleep metric sensor and an activity metric sensor. For example, in addition to measuring the position of the user in bed, a pressure sensor may also measure a minimum amount of depression and a minimum amount of time that the user spends on the sleep system, indicative of the time of duration of the activity "lying in bed."

In some embodiments, the sleep environment may further comprise environmental sensors such as a room temperature sensor, a humidity sensor, an air quality monitor, a noise level sensor, a light intensity sensor, and combinations thereof. Environmental sensors may be installed at predetermined locations within the room, or may be portable.

In the example shown in FIG. 1, sleep environment 105 further comprises a sleep environment controller 140. Such a controller may communicate with some or all of the sleep metric sensors and activity metric sensors to consolidate and pre-process measured data, and further communicate with a server 150 having access to a database 160. Controller 140 may be a general purpose computing device, and it may have user input and output interfaces, as appropriate. Examples include projectors or TVs with input keyboards or touch screens, desktops, laptops, tablets, smartphones, wearable watches, and the like. In some embodiments, sleep environment controller 140 is a dedicated computing device or controller module. In some embodiments, data may be offloaded from sleep environment controller 140 and transferred to server 150 indirectly, as discussed with reference to FIG. 10A.

In different embodiments, server 150 and database 160 may be located within the sleep space, close to the sleep space, remote from the sleep space, or distributively in the cloud. Server 150 may interact with sleep environment controller 140 to collect sleep metric and activity metric measurements from one or more sleeping environments as disclosed herein, at discrete time intervals over a period of time such as overnight, over the span of a given number of hours or days, or over discontinuous intervals such as several nights.

The measured time-series data may be stored in database 160 and analyzed numerically to generate a user report. Such a user report may contain one or more quantitative data points such as the original sleep or activity measurement, and/or may include derived statistics such as user specific statistics and/or population statistics collected over similar sleep environments or similar user cohorts. For example, such a user report may indicate an amount of time the user has spent in the sleeping environment, the percentage of time he or she has spent doing different types of activities, and physical biometric measurements of the user while doing the recorded activities. In some embodiments, the sleep environment management system may detect a location of the user in the sleep environment or sleep space, and/or continuously record an array of coordinates of the user's location within the sleep environment. For example, the user may be identified as on the bed, in front of the TV, near the window, or pacing back and forth between a sofa and the bed. Such location information may be provided in the user report. In some embodiments, physical objects within the sleep environment may be moved in response to the identified user's location, and elements of the sleep environment may be adjusted based on the user's location. For example, a scent and an air quality within the sleep environment may be changed in response to the user's location, and a volume of sound produced by a sound machine may change according to user location as well. In some embodiments, sleep metrics and activity metrics of the user may be correlated across time to predict expected behaviours of the user based on analysis of prior behaviours of the user in similar conditions. In some embodiments, sleep metrics and activity metrics of two or more different users may be correlated across time to predict expected behaviours of a given user based on analysis of prior behaviours of other users in similar conditions. Smart recommendations on sleep-related products may also be provided based on the correlations of sleep metrics and activity metrics from the two or more users across time. Furthermore, a user report may be generated over the given period of measurement, or a shorter timespan within the measurement period. The user report may be updated periodically as more sleep metric and/or activity metric data are collected.

In some embodiments, part or all of such user report is sent back to a user device, where the report is viewable via a user interface, and may be relied on by sleep environment controller 140 as feedback information for adjusting elements of the sleep environment. For example, if it is determined that the user has high body temperature, or rolling-over frequently in light sleep, a room temperature of the sleeping space may be lowered accordingly to help improve the user's sleep quality. In some embodiments, controller 140 also serves as the user device. When the user report is generated based on sleep and activity metric measurements from multiple users, this user report may be viewed as a population report.

In various embodiments, server 150 may receive user permissions to share the user report with a third-party, and subsequently share the user report with the third party, anonymously or otherwise. Exemplary third-parties include, but are not limited to, a medical professional, a medical institute, a sleep environment management agency, or personnel such as a hotel manager, and a salesperson for sleep-related products such as beds, mattresses, and air purification systems.

In some embodiments, the sleep environment may be associated with an entity in which a user can experience the entire sleep environment over at least one night, including hospitality partners, such as, but not limited to, hotels, sleep apnea centers, drug rehab centers, plastic surgery rehabilitation facilities, hospitals, physical therapy rehabilitation centers, and more generally, anywhere a guest would stay more than one night and experience the sleep environment. These hospitality partners may be termed "hospitality partners," "hospitality venues," or "sleep environment providers" in some embodiments.

In some embodiments, health and sales information may be provided to the user by placing or displaying various sleep-related products including at least a bed, an air purification system, and a sound system in the sleeping environment for a substantial period of time, where the period of time may be sufficiently long enough for the user to have a first-hand experience of the sleep environment, and where the user may choose to purchase one or more of the sleep-related products from the sleep environment.

In some embodiments, server 150, or a separate server, houses information on sleep-related products. Such server(s) may be accessible by various third-party agents or stakeholders, who may use a user interface accessible through a computer system to view, add, retrieve, and edit information displayed to the user and information stored in database 160. Some third-party agents such as medical professionals may examine the user reports to evaluate the user's health status, sleep status, and provide either diagnosis or recommendations for further sleep studies. Some third-party agents such as hotel and resort management personnel may examine the user report to understand a particular user's or a group of users' activities within a sleep environment, for improving the design of the sleep environment and the arrangement of objects within the sleep environment. Some third-party agents, or stakeholders, such as a salesperson may use the user interface to advertise, promote, sell, or lease sleep-related products installed in sleep environment 105. By employing the above disclosed system and method, processes may be designed and built with the assumption that it may be possible to assist an agent or stakeholder to handle sleep environment management information in the central server that will be suitable to their respective needs, irrespective of numerous parameters involved in sleep environment management and purchase of sleep-related products.

As an example, in one embodiment of the present invention, the sleep management system and method may assist in placing or displaying different sleep-related products in the sleep environment, based on the generated user report. For example, a new mattress design in a hotel room with best-in-class air purification and noise cancellation technologies may create the ultimate sleep environment in which a user can attain prolonged deep sleep, with steady heart rate, respiratory rate, and a very fresh feeling after waking up. The user may in term be interested in the various sleep-related products including the mattress, the air purification system, and/or the noise cancellation device, each of which may be sold separately to the user directly from the sleep environment controller. In another example, such sleep environments may include luxury sleep systems, that may be placed into a region's hotels, creating the ultimate showroom for such products to be experienced by large volumes of guests, who may then choose to purchase the sleep-related products from the sleep environment for their individual uses.

Figure 2:
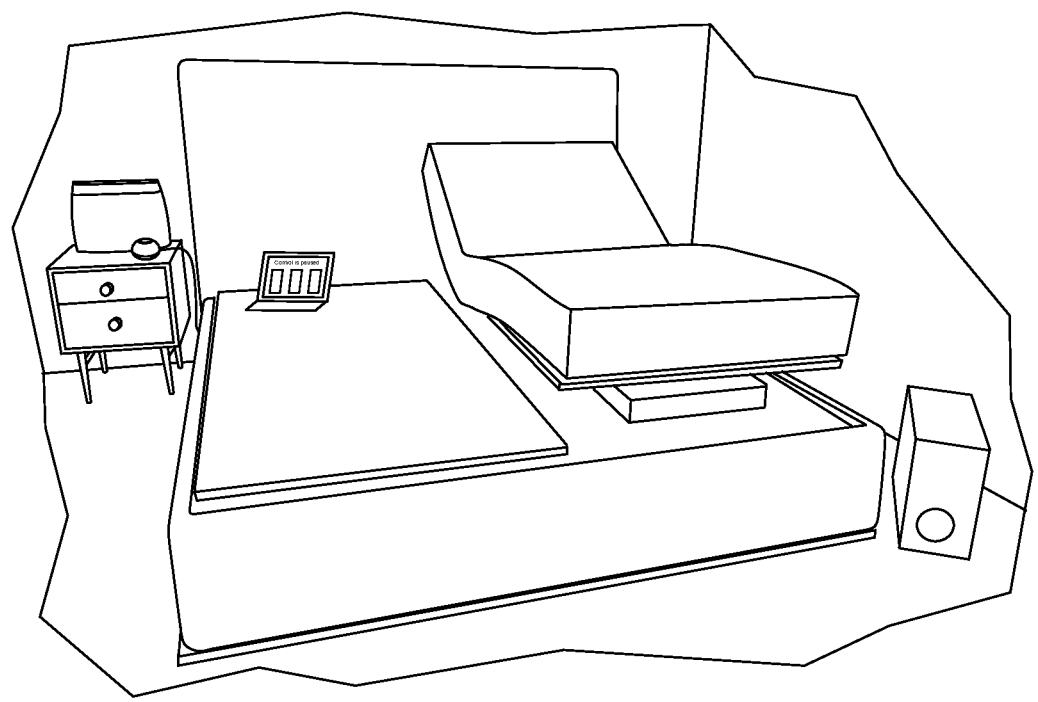
FIG. 2 shows a perspective view of an exemplary sleep environment, positioned inside a hotel room, according to one embodiment of the present invention.

FIG. 2 shows a perspective view 200 of an exemplary sleep environment, according to one embodiment of the present invention. Such a sleep environment may be located within a hotel, a medical facility, or the like. This exemplary sleeping environment comprises a bed, an air purification device and a sound machine located on the night stand, a user computing device positioned on the bed, and a server placed at the foot of the bed. While not shown explicitly, a sleep environment controller, in the form of a stand-alone computing device or an app on the user device, interacts with each of the electronic devices within the sleep environment to collect data and provide control instructions. In some embodiments, the sleep environment may further comprise a dynamic lighting system, and a dynamic audio system in place of or in addition to the sound machine. In one embodiment, the sleeping environment may utilize slatted, kinetic foundations in conjunction with the latest in mattress technology, to give users a perfectly anatomically-aligned, temperature-controlled, and pressure-relieving night's rest. The sleep environment may chemically-free purify the air, and sanitize the room to create a virus/bacteria/mold-free, odor-free, and hypo-allergenic environment. Further, the sound machine may be used for sound generation, suppression, and reduction. For example, it may generate a white noise, a sound masking noise, music, radio broadcast, audio reading, and/or noise cancellation for an improved sleep environment. A comprehensively optimal room environment may then be created for a user's senses, to facilitate healthy, comfortable, and rejuvenating sleep, as well as facilitate the sales process.

Furthermore, in some embodiments, by placing state-of-the-art bedding, air purification units, and sound machines within hotels, resorts, and villa properties, with no required capital investment to the property owners, use of these properties may significantly reduce capital expenditures and sales operating costs, increase room rates, differentiate and upgrade their brand, and offer users or guests the healthiest sleep experience possible. Accordingly, the method for sleep environment management may further include placing sleep-enhancing environments into the luxury hospitality market by building strategic partnerships with hoteliers, creating a venue for qualified guest-customers to purchase unique products from "hotel-to-home."

Figure 3:
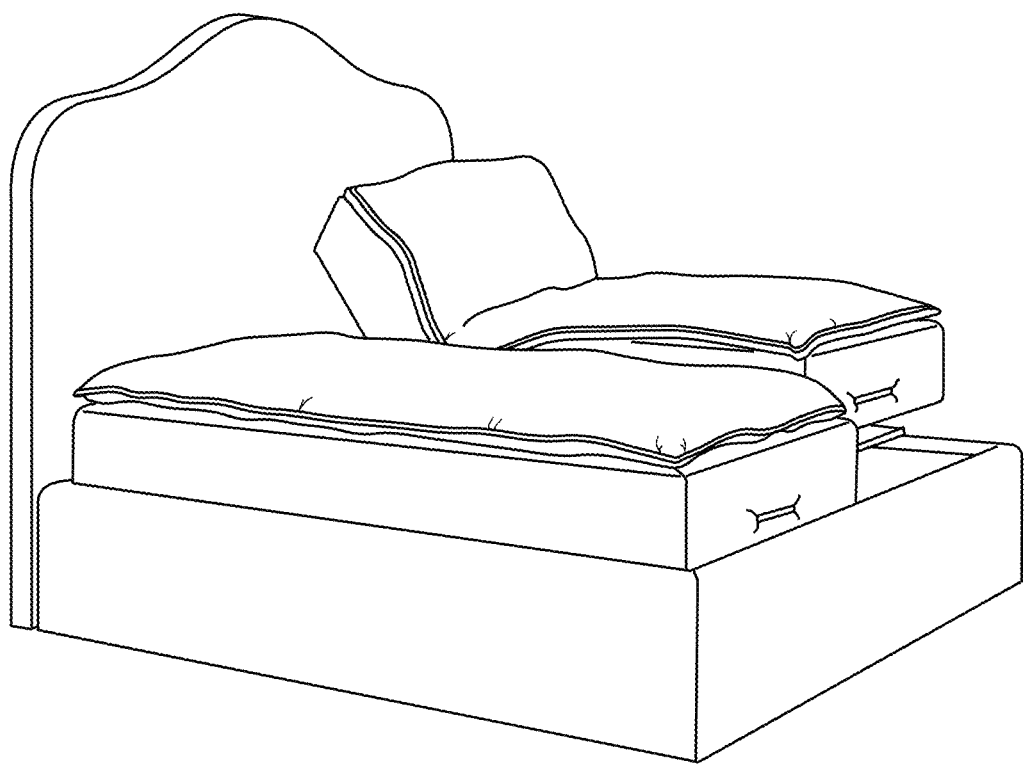
FIG. 3 shows a perspective view of an exemplary bed within the sleep environment, according to one embodiment of the present invention.

FIG. 3 shows a perspective view 300 of an exemplary bed, according to one embodiment of the present invention. In this exemplary embodiment, the bed in the sleep environment is a "Pressure Balance Sleep" system (PBS™) manufactured by I-Bedding SRL (hereafter, I-Bedding or NOT-TINBLU™). This product represents a revolutionary technology and is a marked advantage over traditional spring mattresses, memory foam bedding, and air chamber technologies. The PBS™ bedding systems may address and correct all of the problems inherent in current industry-standard bedding technologies. The comprehensive "Sleep Systems" utilizes slatted, kinetic foundations in conjunction with the latest in mattress technology, to give users a perfectly anatomically-aligned, temperature-controlled, and pressure-relieving night's rest.

Figure 4:
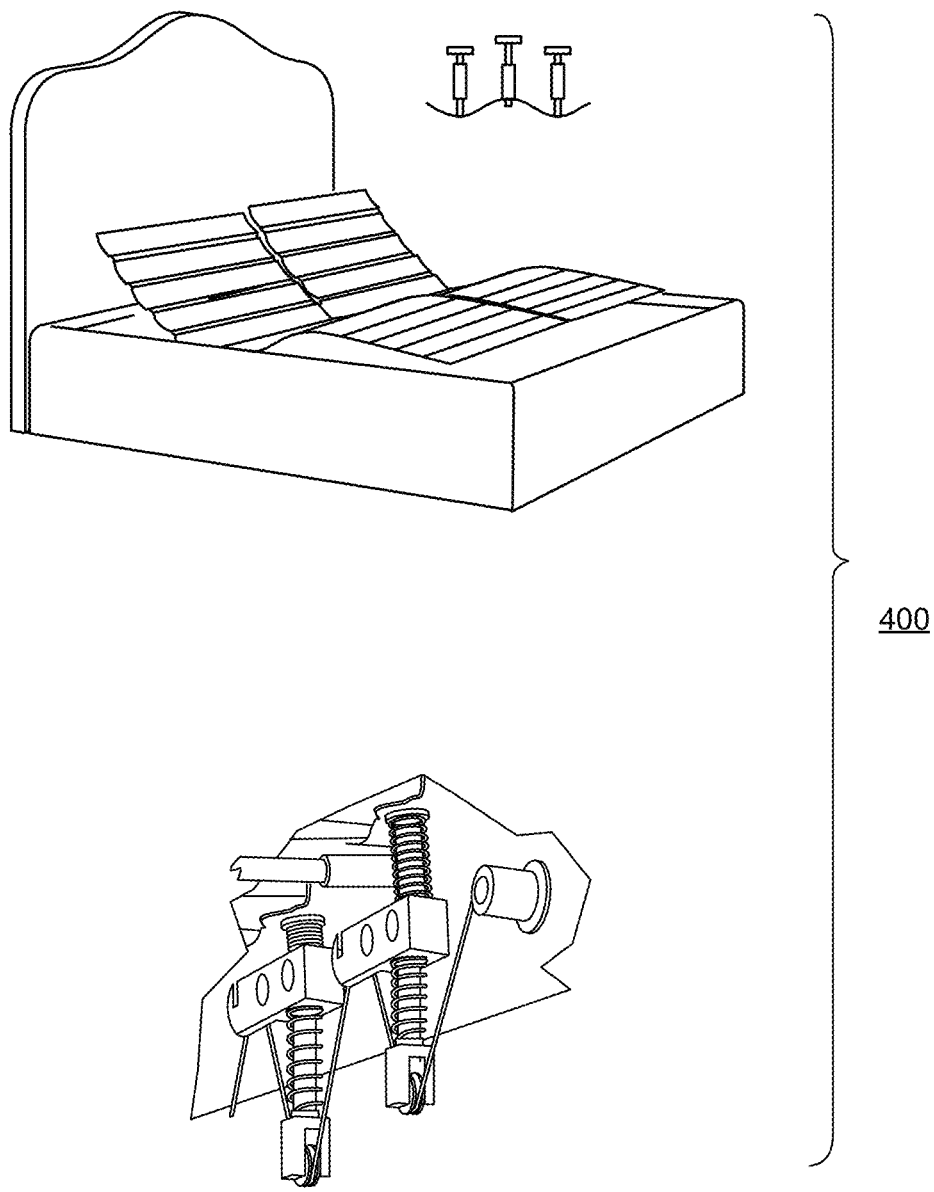
FIG. 4 shows a schematic of the exemplary bed within the sleep environment, adjustable via an underlying spring system, according to one embodiment of the present invention.

FIG. 4 shows a schematic 400 of the exemplary bed in FIG. 3, adjustable via a underlying spring system, according to one embodiment of the present invention. In this exemplary embodiment, the bed may include a self-regulating sleep system that may correct orthopaedic support of the spine, regardless of the user's weight, height, and sleep position. The sleep systems may deliver a highly personalized sleep experience, with a continuously self-adjusting bed. The sleep system may feature slats resting on a series of pistons interconnected by a pre-stressed steel cable which balances and supports the body evenly by distributing the user's weight. By delivering muscular relaxation and optimal spinal alignment, thermoregulation, hygiene, and unsurpassed comfort throughout the night, the sleep system may provide good sleep to the user. The sleep system may include features including, but not limited to, individual support and comfort in any sleeping position, optimal spinal alignment, optimum pressure relief and body conformation, a dry and hygienic sleeping climate achieved through the excellent breathability of materials, organic and pure "environmentally friendly" materials employed, suitability for and beneficial to allergy sufferers, durability, less motion disturbance, no "roll together" between sides, different comfort choices in one mattress, component engineering for replacement rather than obsolescence, among other features. The articulating electric models of the sleep systems may be supplied with a micro-computer that may recall the user's favourite positions, for example, sitting up for reading, watching TV, etc., with the simple press of a button.

In some embodiments, the sleep system may include a mattress cover made of virgin wool, which may be antibacterial and antimicrobial. Wool naturally wicks away moisture from the body, helping to maintain a neutral body temperature which stabilizes the body's thermoregulation during sleep. Other product categories in the sleep environment may include linens, pillows, white noise generators, and hydroxyl air purification systems that comprehensively allow the guest to experience an optimal room and sleeping environment.

One of ordinary skill in the art will recognize that the present invention is not limited to utilization with the PBS™ bed or sleep system, and any sleep system, bed, and bedding technology may be placed and sold via the methods and processes described herein. One of ordinary skill in the art will also recognize that the present invention is not limited to utilization with these particular sleep system components listed, and any sleep system component or sleep technology (e.g., snoring aids, surround sound machines, televisions, etc.) may be placed and sold via the methods and processes described herein.

Figure 5:
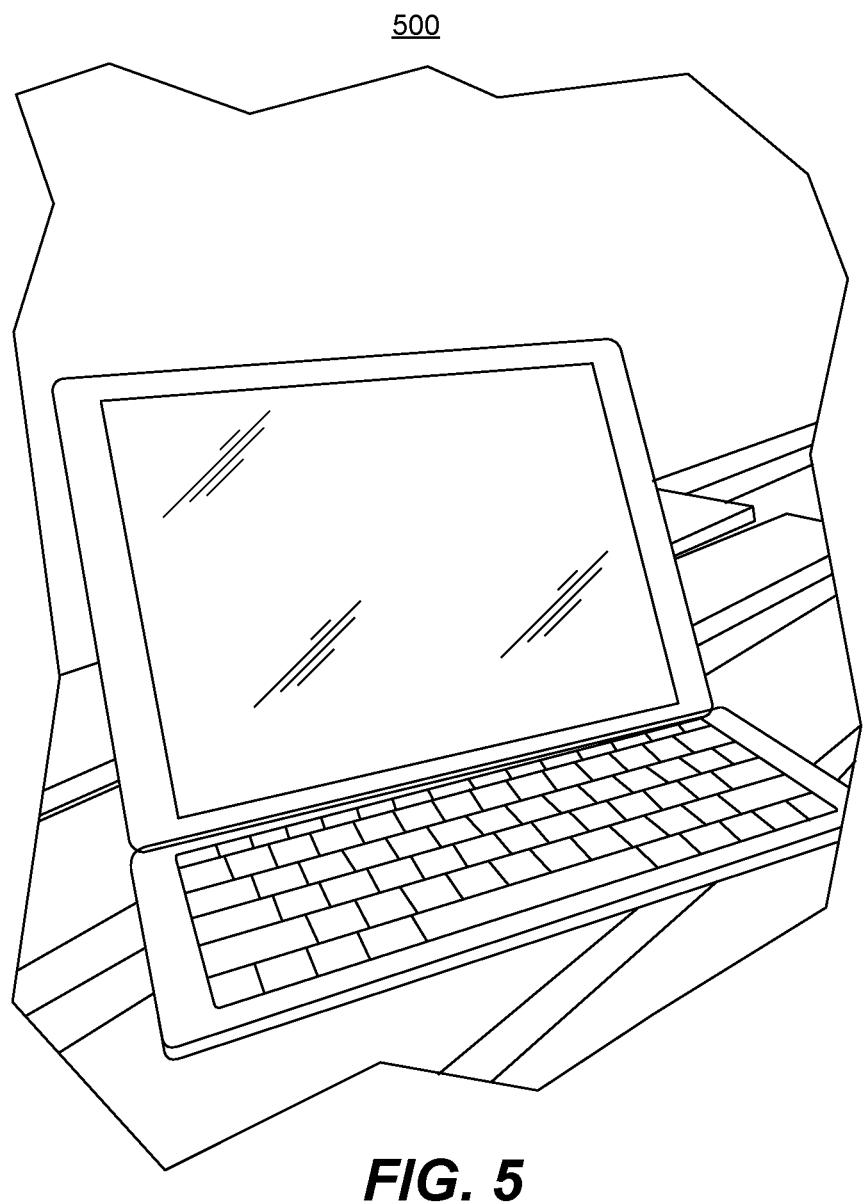
FIG. 5 shows a view of an exemplary computing device, according to one embodiment of the present invention.

FIG. 5 shows a view of an exemplary computing device 500, according to one embodiment of the present invention. More details on the technical implementation of such a computing device is provided in reference to FIGS. 13 and 14. In this particular example, the computing device is a tablet computer. The computing device may serve as a sleep environment controller to control the sleep environment management system, or as a user device to interact with the user of the sleep environment, or serve both purposes at the same time.

The sleep environment controller functions as a base station to control or configure electronic devices within the sleep environment. In some embodiments, the sleep environment controller may comprise an adaptive environmental digital product library logic module, which controls the environmental conditions within the sleep environment. Such environmental conditions may comprise temperature, humidity, noise level, light intensity, and the like. Measured environmental conditions may be provided to the server for storage in the database along with the sleep metric and the activity metric measurements.

A user device in the context of the sleep environment may perform various user-specific functions in different embodiments of the present invention. In some embodiments, the user device contains input and output user interfaces. For example, input to receive user permission for sharing sleep data with third parties. In some embodiments, the user device is connected to a communication channel linked to a server, wherein the user interface is used by third-parties or stakeholders for advertising, selling, browsing, and/or purchasing sleep-related products from the sleep environment, and wherein the server houses information on the sleep-related products. In some embodiments, the user device receives input from the user from a universal remote, and presents information to educate the user with features of sleep-related products. In some embodiments, user-specific input is also received via the user device, where such user-specific feedbacks may be correlated using a series of pre-defined weights and tolerances to collect, interpret, and analyze sleep habits associated with the user. In some embodiments, the user device is physically separated from but operatively connected to the sleep environment controller. In some embodiments, the user device comprises the sleep environment controller. For example, the sleep environment controller may be a software application installed on a general purpose portable computer.

In some embodiments, the sleep environment controller and/or the user device further comprises a voice-enabled interface, which in turn comprises a voice-enabled device adapted to receive voice commands from a user.

Figure 6:
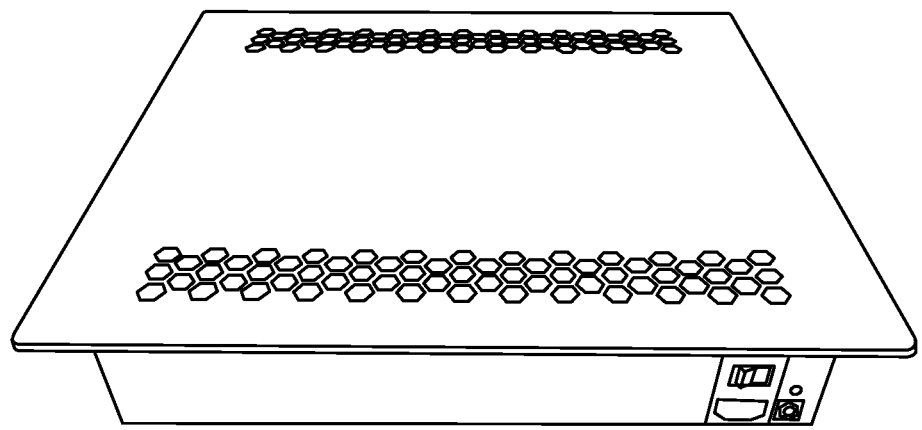
FIG. 6 illustrates an exemplary air purification unit used in the sleep environment, according to one embodiment of the present invention.
Figure 7:
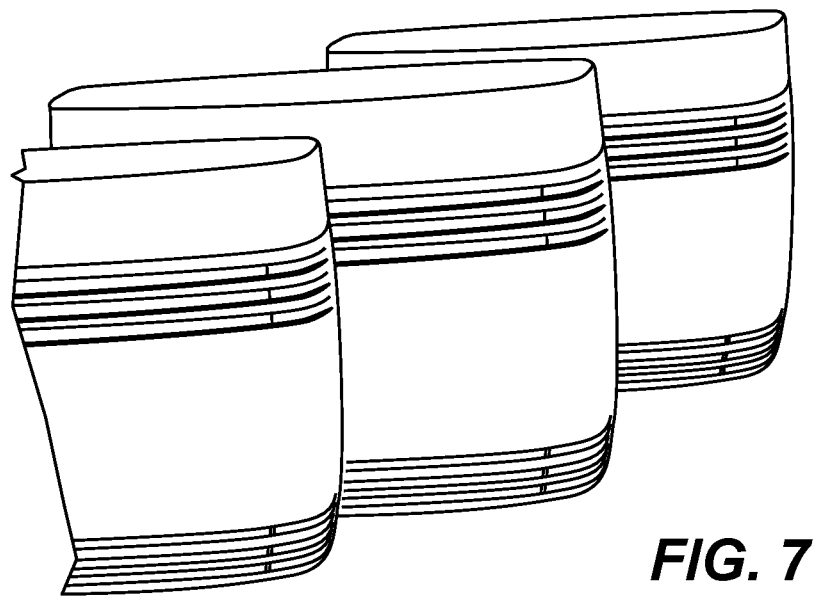
FIG. 7 shows another exemplary air purification unit used in the sleep environment, according to one embodiment of the present invention.

FIG. 6 illustrates an exemplary air purification unit 600 used in the sleep environment, according to one embodiment of the present invention. FIG. 7 shows another exemplary air purification unit 700 used in the sleep environment, according to another embodiment of the present invention. In some embodiments, the air purification unit is selected from the group consisting of a hydroxyl generator, a photocatalytic oxidation (PCO) system, an ozone generator, and an ultraviolet (UV) light system. In one embodiment, the air purification unit may include hydroxyl generators. Hydroxyls are safe, naturally occurring molecules, which are created constantly in the outdoor atmosphere when the ultraviolet rays of the sun react with water vapor from the air. Hydroxyls are the single most important agent that scrubs and cleanses the planet's atmosphere. However, indoors, without direct sunlight, the interior atmosphere does not naturally receive the benefit of hydroxyls. Hydroxyl generators will neutralize odors, allergens, viruses, mold, and bacteria on all surfaces and in the atmosphere of a room environment, creating the cleanest, safest, and purest air within the sleep environment. For example, the air purification unit can be used to reduce the labour and operating expenses associated with cleaning and turning over hospitality rooms after utilization by guests due to the increased concern about COVID-19.

Figure 8:
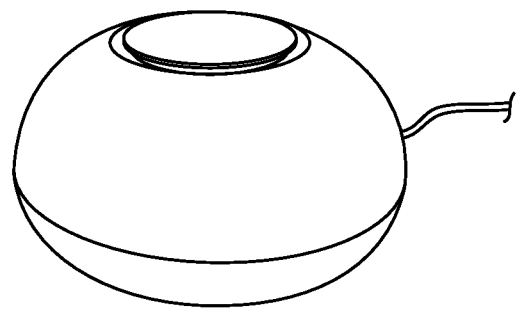
FIG. 8 shows an exemplary sound machine used in the sleep environment, according to one embodiment of the present invention.

FIG. 8 shows an exemplary sound machine 800 used in the sleep environment, according to one embodiment of the present invention. In some embodiments, the sound machine may be used to help users fall asleep faster, sleep more deeply, and stay asleep longer, reducing auditory sensory input to an over-stimulated mind, drowning out noise, and promoting optimal brain waves to achieve rejuvenating sleep. In various embodiments, the sound machine may generate white noise, a sound masking noise, music, radio broadcast, audio reading, and noise cancellation for an improved sleep environment. In some embodiments, the sound machine is a software module accessible by the sleep environment controller.

Figure 9:
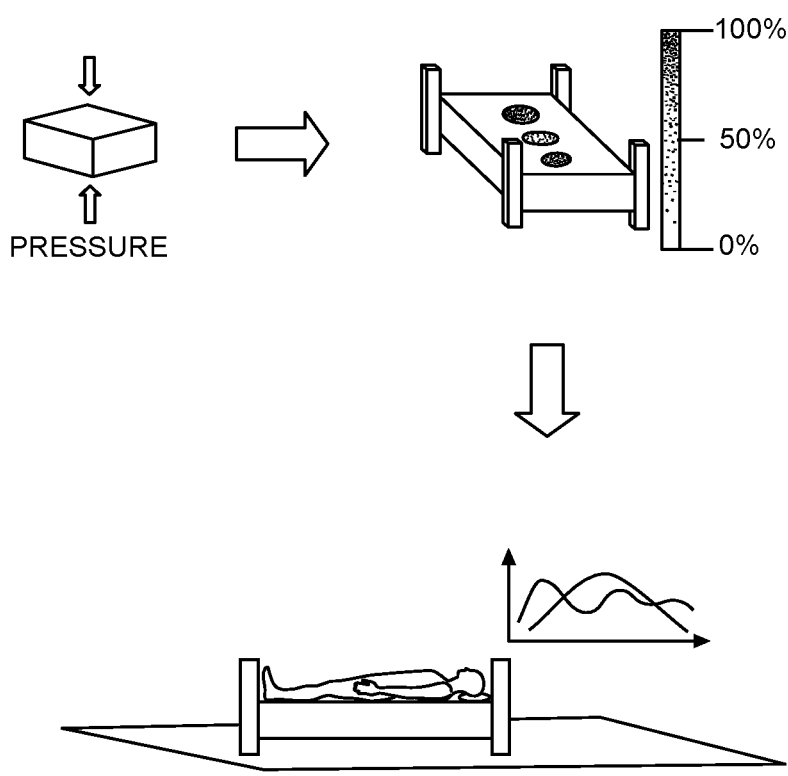
FIG. 9 shows a schematic illustrating use of pressure sensors for sleep metric measurements, according to one embodiment of the present invention.

FIG. 9 shows a schematic 900 of using pressure sensors for sleep metric measurements, according to one embodiment of the present invention. A pressure sensor has a sensing element of constant area and responds to force applied to this area by external pressure. Magnitude of this applied force may be converted into an electrical output signal, and correlates to both time and position of a user on the bed. Multiple correlating pressure sensor readings may indicate the duration and position a user spends on the bed, as well as the motions of the user while in bed. In some embodiments, the pressure sensors may be installed within the mattress. In some embodiments, the pressure sensors may be ultrathin tactile sensor arrays easily weaved into bedsheets or mattress covers. Such tactile sensor arrays may be flexible, conformable, and may cover a large total area with a very fine sensor resolution in each measurement area. Most importantly, they may be entirely unnoticeable to the user. In some embodiments, artificial intelligence (AI) based algorithms and/or machine learning algorithms may be implemented in connection with the disclosed pressure sensors to detect movement and position of the user while lying in bed or sleeping.

Figure 10A:
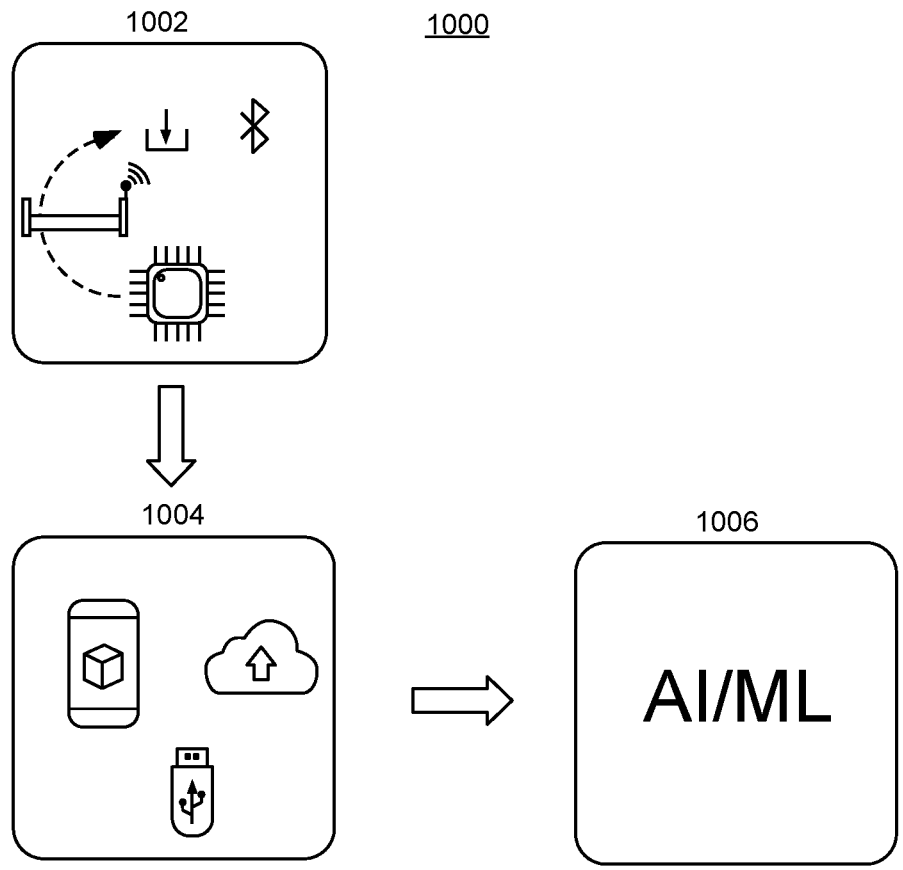
FIG. 10A shows a schematic of an artificial intelligence (AI) system for sleep environment management, according to one embodiment of the present invention.

FIG. 10A shows a schematic 1000 of an artificial intelligence (AI) system for sleep environment management, according to one embodiment of the present invention. In particular, FIG. 10A illustrates an example flow of communication and data between the disclosed sleep metric sensors and/or activity metric sensors and one or more peripheral devices, according to some embodiments of the present invention. In some embodiments, data may be offloaded from a sensing device by wired or wireless connection 1002. In some embodiments, wired connection (e.g., USB) may be used to download data, for possible offline processing. In some embodiments, a wireless connection may be used via any suitable air interface such as, WiFi and/or Bluetooth, to transfer data from the sensing device to the user device or a central base station. In different embodiments, sensed data may be stored, analyzed, and shared using multiple online and offline methods 1004. In another embodiment, sensed data may be transferred to an app on a computing device, uploaded and transferred via USB, or stored in the cloud. Moreover, sensed data may be managed and analyzed using a server 1006 running one or more artificial intelligence (AI)-based algorithms to monitor sleep metric and activity metric data. Such AI-based algorithms may learn from the user's behaviors and recognize patterns of changes in the user's movement before, during, and after sleep. Various AI and machine learning (ML) algorithms are within the scope of the present invention, including but not limited to neural networks, deep learning networks, Bayesian belief nets, classification and regression trees, decision trees, and so forth. The ML algorithms may be used to extract useful intelligence from the sleep metric and activity metric data automatically, without operator intervention. The ML algorithms can look for patterns or correlations in the user's sleep patterns from the sleep metric sensors based on factors within the sleep environment, such as the environmental conditions in the sleep environment, time of sleep initiation, activities performed before sleep, and so forth. The ML algorithms may then provide smart recommendations to the user for improving their sleep quality and/or quantity. In some embodiment, the ML algorithms may also receive one or more product parameters of one or more physical products in the sleep environment, and provide one or more product recommendations to the user by correlating the sleep metrics, the activity metrics, and the one or more product parameters.

Figure 10B:
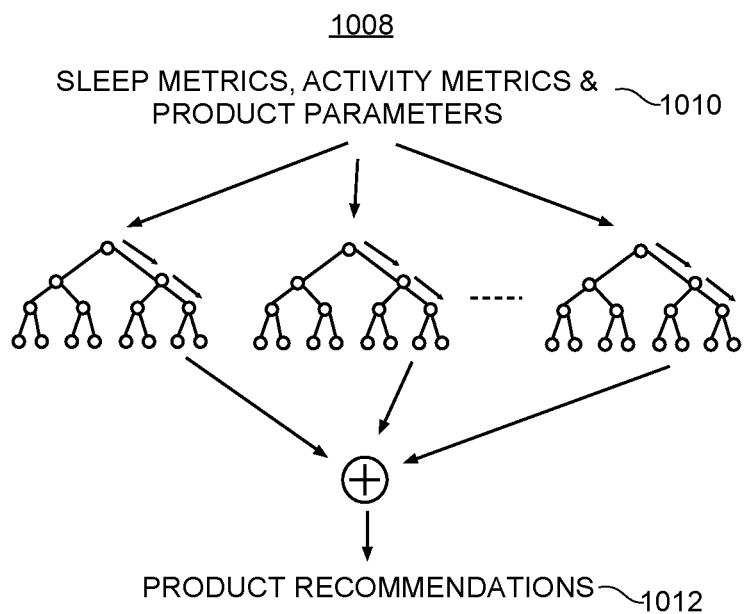
FIG. 10B shows an illustrative diagram for a machine learning (ML) module for one or more product recommendations from one or more sleep metrics, one or more activity metrics, and one or more product parameters, according to one embodiment of the present invention.

FIG. 10B shows an illustrative diagram 1008 for a machine learning (ML) module for generating one or more product recommendations from one or more sleep metrics, one or more activity metrics, and one or more product parameters, according to one embodiment of the present invention. FIG. 10B shows one or more sleep metrics, one or more activity metrics, and one or more product parameters as the input feature vector 1010. That is, the input to the ML module is the one or more sleep metrics, the one or more activity metrics, and the one or more product parameters 1010. The output of the ML module is one or more product recommendations 1012.

In one embodiment, shown schematically in FIG. 10B, the ML module uses a random forest algorithm, which is an illustrative machine learning algorithm. The random forest algorithm uses a multitude of decision tree predictors, such that each decision tree depends on the values of a random subset of the training data, which minimizes the chances of overfitting. In one embodiment, the random forest algorithm is implementation as described in Leo Breiman, Random Forests, Machine Learning, 45, 5-32, 2001, Kluwer Academic Publishers, Netherlands, Available at doi.org/10.1023/A:1010933404324, which is hereby incorporated by reference in its entirety as if fully set forth herein. The random forest algorithm is only one illustrative machine learning algorithm that is within the scope of the present invention, and the present invention is not limited to the use of random forest.

It may be appreciated that random forests are selected in the examples above as the ML module algorithm by way of illustration and not limitation, and that other ML algorithms can be implemented for the ML module such as, but not limited to, other linear and non-linear regressors, such as K-means clustering and Support Vector Machines (SVMs), in accordance with the examples disclosed herein. A simple linear regressor, such as a correlation coefficient, may also be utilized in some embodiments. The correlation coefficient may simply correlate the one or more product recommendations with the sleep and activity metrics. Other machine learning algorithms, including but not limited to, nearest neighbor, decision trees, support vector machines (SVM), Adaboost, Bayesian networks, various neural networks including deep learning networks, evolutionary algorithms, and so forth, are also within the scope of the present invention for implementing the ML module.

In some embodiments of the present invention, the ML module is trained on ground truth data comprising one or more product recommendations and one or more sample feature vectors for one or more sample users' sleep and activity metrics.

As noted, embodiments of devices and systems (and their various components) described herein can employ artificial intelligence (AI) to facilitate automating one or more features described herein (e.g., providing sleep product recommendations, and the like). The components can employ various AI-based schemes for carrying out various embodiments/examples disclosed herein. To provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc.

from a set of observations as captured via events and/or data. Determinations can be employed to identify a specific context or action, or can generate a probability distribution over states, for example. The determinations can be probabilistic—that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform a number of functions, actions, and/or determinations.

A classifier may map an input feature vector (e.g., sleep and activity metrics) to a confidence level that the input belongs to a class, such as a product recommendation. Such classification may employ a probabilistic and/or statistical-based analysis (e.g., factoring into the analysis utilities and costs) to determinate an action to be automatically performed. Various directed and undirected model classification approaches include, e.g., support vector machines (SVMs), naive Bayes, Bayesian networks, decision trees, neural networks, fuzzy logic models, and/or probabilistic classification models providing different patterns of independence can be employed. Classification as used herein also is inclusive of statistical regression that is utilized to develop models of priority. In short, various machine learning methods, algorithms, and modules are within the scope of the present invention.

Illustrative Embodiment of Sleep Environment Management System in Hospitality Settings In various embodiments, the user may be familiarized with the sleep environment and the sleep-related products at various stages of the user's stay in the sleep environment. In a first step, before the stay, the sleep environment provider may attempt to understand from the user's standpoint the single most important element of the guest room, the bed. The user will be provided access to the computer system that may identify to the user that they will be sleeping on a sleep system that is the finest in the industry, and that the overall room environment has been comprehensively outfitted to provide the highest levels of health and comfort. In a second step, during the stay, marketing and brand awareness will be delivered via the computer system, for example, through a tablet with a proprietary app, custom-tailored to the sleep environment provider, that may be part of the room amenities. This tablet, custom-loaded with unique-to-the-guest communications, may act as both a sleep environment controller and education center for the room. It may also wirelessly control all articulating bed functions, adjust the hydroxyl generator levels, control room thermostat functions, and seamlessly deliver product marketing videos in a non-intrusive fashion. These videos, tailored to the sleep environment provider in which the guest is staying, will detail the practicality and function of the in-room systems installed in the room, to the great benefit of the guest experience. In one embodiment, this computer system will also be the portal for the products and sell-through program. In a third step, after the stay, the guest may decide to purchase a sleep-related product. If purchased, the purchase may come from the sleep system provider; and in one embodiment may include a money back guarantee and a comprehensive warranty, further facilitating the sales process.

In some embodiments, partnering with a sleep environment provider renders the sleep environment provider, for example, the hospitality venue into a showroom, eliminating the need and capital for "brick and mortar" stores. Partnering with hotels and resorts presents opportunities on two fronts. The first is the ability to place significant quantities of sleep-related products in hotels and resorts at one time, and thereby expose very large volumes of prequalified customers to such products. The second is allowing guests to experience the bedding and other in-room sleep-related products, and make purchases of the products for their personal use directly through the hospitality partner website using the computing system located directly in the hotel room, at their own comfort and without the presence of salespeople.

In some embodiments, the sleep environment providers, e.g., hotels and other venues, may significantly reduce capital expenditures and property operating costs, increase room rates, differentiate and upgrade their brand, and offer guests the healthiest sleep experience possible. In one embodiment, these environmental upgrades may be provided by financial partners, who invest in these furnishings via debt financing that return a significant financial return (e.g., 9-12% interest over their five-year term). This asset-backed (the sleep systems themselves) return may be supported by a contract between a sleep-related products provider and the sleep environment providers with a historical track record of known occupancy rates and successful operations. The installation of these sleep-related products with the sleep environment provider may help increase the revenue for the sleep-related product provider. Advantageously, the model may create winning propositions for all parties involved: sleep-related products manufacturers, the sleep environment user, the sleep environment provider, the financial partner, and the sleep environment company.

In some embodiments, the sleep environment management system may be set up using the following steps. In a first step, the sleep-related products provider may approach a sleep environment provider. In a second step, the sleep-related products provider may offer to place state-of-the-art sleep systems, bedding, air purification units, and white noise machines in a space provided by the sleep environment provider at no cost to the sleep environment provider based on a mutual agreement. A sleep environment user may be provided with a system to purchase sleep-related products of the types placed in the sleep environment. In one embodiment, a sleep environment user may be provided with a system to purchase sleep-related products placed in the sleep environment and used by them in the sleep environment setting.

The sleep environment management system as disclosed herein is described in a hospitality setting, as an illustrative embodiment of the present invention. In this particular embodiment of this invention, systems and methods for sleep environment management further allow interaction with sleep environment users, who are potential customers to sleep-related products in the sleep environment.

Figure 11:
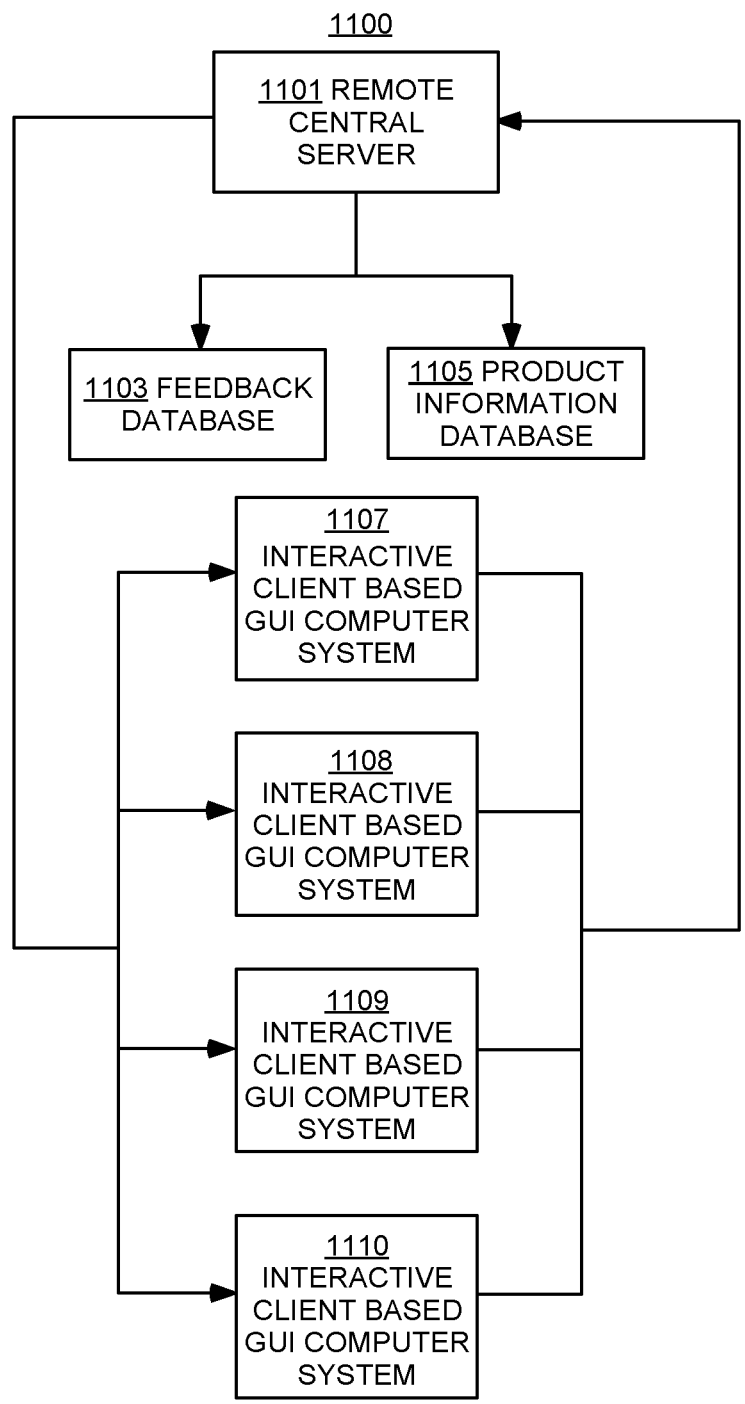
FIG. 11 illustrates an example of a network, comprising a remote central server, feedback database, and product information database connected to various clients at different illustrative locations, according to one embodiment of the present invention.

FIG. 11 illustrates an example of a network 1100, comprising a remote central server 1101, feedback database 1103, and product information database 1105 connected to various clients 1107, 1108, 1109 and 1110 at different illustrative locations. The network may comprise Ethernet cable, wireless, or fiber optics to transmit data between each node, as would be recognized by one of ordinary skill in the art.

Figure 12:
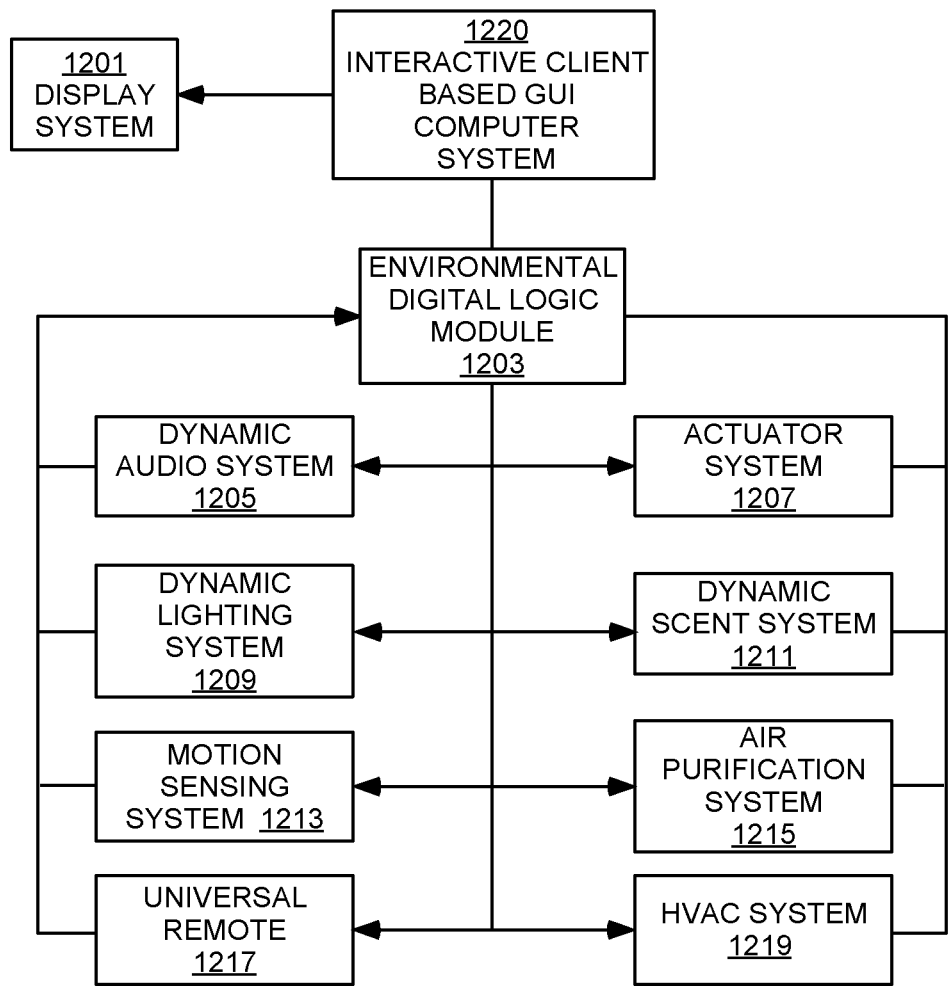
FIG. 12 illustrates an exemplary environmental digital logic module, according to one embodiment of the present invention.

FIG. 12 shows a diagram 1200 illustrating an environmental digital logic module 1203 for controlling the environmental conditions within the sleep environment, according to one embodiment of the present invention. In this system, environmental digital logic module 1203 interacts with an interactive client based GUI computer system 1220 which has access to a display system 1201. In different embodiments, environmental digital logic module 1203 may further interface with one or more of a dynamic audio system 1205, a dynamic lighting system 1209, a motion sensing system 1213, a universal remote 1217, an actuator system 1207, a dynamic scent system 1211, an air purification system 1215, and an HVAC system 1219.

In this example, interactive client-based graphic user interface (GUI) computer system 1220 utilizes environmental digital logic module 1203 to interact with the user's five senses to create a highly intelligent control system. In some embodiments, interactive client-based graphic user interface (GUI) computer system 1220 is a user computing device with a user interface for viewing sensor measurements and statistics, and for receiving user input and instructions for sleep environment management. Environmental digital logic module 1203 includes a combination of computer hardware and software to process information to and from the systems within a hotel room sleep environment. The intelligence of the environmental digital logic module 1203 relies on a software-based system that analyzes data received by the sensors within the sleep environment and weights the data based on predefined settings. These settings and tolerances may be adjusted by an administrator remotely from a web based client or onsite via a graphic user interface. The control and feedback of the room allows an administrator to make adjustments to improve the end-user sleep experience. If a system within the room experiences technical difficulties, the digital logic module provides alerts to notify a list of contacts via email and telephone of any technical problems of specific components and conditions within the room.

In some embodiments, the sleep system comprises at least a sensor that measures whether the guest has actually stayed in the room. In one embodiment, the sensor is a pressure sensor that measures a minimum amount of depression and a minimum amount of time that the guest spends on the sleep system. In some embodiments, the sensor ties into other data sources and sensors in the room, that together create a holistic picture of the sleep quality, sleep experience, and general experience of the guest with the sleep system. This provides unique insights into the guest, which the system can then correlate with other data about the guest in order to generate a more personalized service plan, as well as additional sales presentation, sales information, or transmit the information to the front desk for service follow-up, or a sales agent for an in-person pitch. As an added benefit, the system may provide feedback on the quality of the sleep to both the guest and the sleep environment provider, e.g., the hotel management.

In one embodiment, motion sensing system 1213 comprising motion sensors allows environmental digital logic module 1203 to determine the location of the user, and adaptively control other systems within the hotel room based on pre-programmed assignments. Motion sensing system 1213 may also provide security to eliminate tamping and theft within the hotel room when the user is away.

In one embodiment, the sleep environment further comprises dynamic audio system 1205 having a set of speakers' pre-manufactured in the ceiling panels, hidden microphones, and a receiver. The environmental digital logic module 1203 connects to the receiver to control which sounds are to be produced based on a set of predefined logic assigned in the software. The microphone provides digital logic module 1203 information to make audio settings adjustments and provide audio systems performance updates to signal that the sounds produced is within a set of predefined tolerances. This microphone may also help indicate data from other systems. For example, if an air circulation fan's ball bearing wear out and produced a loud noise, the microphone may signal to digital logic module 1203 that a strange sound outside of the tolerance range should be examined. Another example is if a guest presses an open button for an entrance door to the hotel room, the actuator system may open a door and transmit a signal through environmental digital logic module software to start playing an introduction program through the dynamic audio system that would greet the user and welcome them into the interactive environment.

In one embodiment, actuator system 1207 may physically control objects within the hotel room based on software programming within environmental digital logic module 1203. For example, if the user enters the room, and lies on the bed, motion sensing system 1205 may transmit a signal to environmental digital logic module 1203 to automatically start an actuator behind a large display to extend it out and angled towards the user. The actuators may also open and close the doors used in the hotel room based on the input received by environmental digital logic module 1203.

In one embodiment, dynamic lighting system 1209 receives inputs from environmental digital logic module 1203 based on pre-programmed software to adjust the brightness and colour of the lighting in the room to help stimulate a positive mood of the user. For example, once environmental digital logic module 1203 notices that a user walks into the room, the lightning system may start a program to implement a series of dazzling lighting effects, and then dim the lighting whenever environmental digital logic module 1203 notices that the user has entered the bed.

In one embodiment, dynamic scent system 1211 and air purification system 1215 adaptively changes the smell of the room based on a theme selected through environmental digital logic module 1203. Scent system 1211 may comprise an aroma-producing solution that utilizes an effect to help enhance the total experience of the guest by transmitting a message to the guest's limbic system which then interacts with his or her memory and emotions. The dynamic scent and air purification systems may be integrated within the air circulation duct that works with the circulation system in the plenum space to ensure that the hotel room smell and temperature are within the tolerances defined in the environmental digital logic module.

In one embodiment, display system 1201 is provided as part of the sleep environment, including one or more screens, which may comprise a combination of LCDs, Plasma screens, projectors, or any output device used to present information in a visual form. The display may help provide a cinematic effect along with a graphic user interface to not only interact but also educate the end-user with information regarding the various products available for purchase. The same display, if needed, may also provide an administrator with a separate graphic user interface to make adjustment to settings and various tolerances in each system within the hotel room.

Computing Device Architecture

Figure 13:
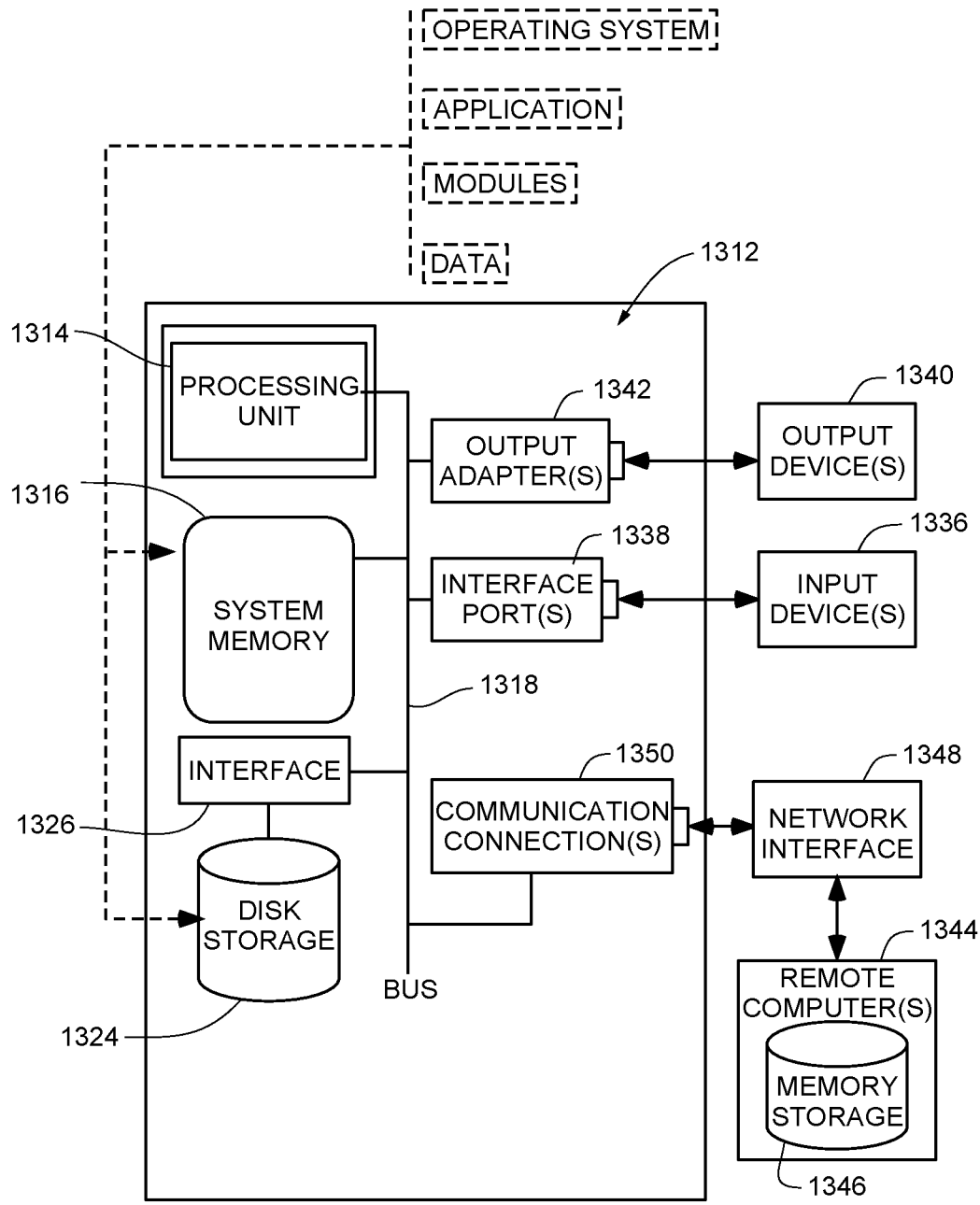
FIG. 13 shows a diagram of an exemplary computational environment for the electronic devices described herein, according to one embodiment of the present invention.

FIG. 13 shows a diagram of an example computational environment 1300 for the electronic devices described herein, according to one embodiment of the present invention. FIG. 13 is intended to provide a general description of a suitable computing environment 1300 in which the various aspects of the system as disclosed can be implemented. FIG. 13 illustrates a block diagram of an exemplary, non-limiting operating environment 1300, including a computing device 1312. The computing device 1312 may include a processing unit 1314, a system memory 1316, and a system bus 1318. System bus 1318 may operably couple system components, and may be any of several types of bus structures including the memory bus or memory controller, a peripheral bus or external bus, and/or a local bus using any variety of available bus architectures including, but not limited to, Industrial Standard Architecture (ISA), Peripheral Component Interconnect (PCI), Universal Serial Bus (USB), Advanced Graphics Port (AGP), Firewire, and Small Computer Systems Interface (SCSI). Computing device 1312 can also include removable/non-removable, volatile/non-volatile computer storage media. FIG. 13 illustrates, for example, a disk storage 1324. Disk storage 1324 can also include, but is not limited to, devices like a magnetic disk drive, floppy disk drive, tape drive, Jaz drive, Zip drive, LS-100 drive, flash memory card, or memory stick. FIG. 13 also depicts software that can act as an intermediary between users and the basic computer resources described in the suitable operating environment 1300. Such software can also include, for example, an operating system for controlling and allocating resources of the computing device 1312, system applications, program components, and program data. It is to be appreciated that this disclosure can be implemented with various operating systems or combinations of operating systems. A user enters commands or information into the computing device 1312 through one or more input devices 1336. Input devices 1336 may include, but are not limited to, a pointing device such as a mouse, trackball, stylus, touch pad, keyboard, microphone, joystick, game pad, satellite dish, scanner, TV tuner card, digital camera, digital video camera, web camera, sensors mentioned above, and the like. These and other input devices can connect to the processing unit 1314 through the system bus 1318 via one or more interface ports 1338. One or more output devices 1340 can use some of the same type of ports as input device 1336. Thus, for example, a USB port can be used to provide input to computing device 1312, and to output information from computing device 1312 to an output device 1340. Output adapter 1342 can be provided to illustrate that there are some output devices 1340 like monitors, speakers, and printers, among other output devices 1340, which require special adapters.

Computing device 1312 can operate in a networked environment using logical connections to one or more remote computers, such as remote computer 1344. The remote computer 1344 can be a computer, a server, a router, a network PC, a workstation, a microprocessor based appliance, a peer device or other common network node and the like, and typically can also include many or all of the elements described relative to computing device 1312. Remote computer 1344 can be logically connected to computing device 1312 through a network interface 1348 and then physically connected via communication connection 1350. Further, operation can be distributed across multiple (local and remote) systems. One or more communication connections 1350 refers to the hardware/software employed to connect the network interface 1348 to the system bus 1318. While communication connection 1350 is shown for illustrative clarity inside computing device 1312, it can also be external to computing device 1312. The hardware/software for connection to the network interface 1348 can also include, for exemplary purposes only, internal and external technologies such as, modems including regular telephone grade modems, cable modems and DSL modems, ISDN adapters, and Ethernet cards.

Figure 14:
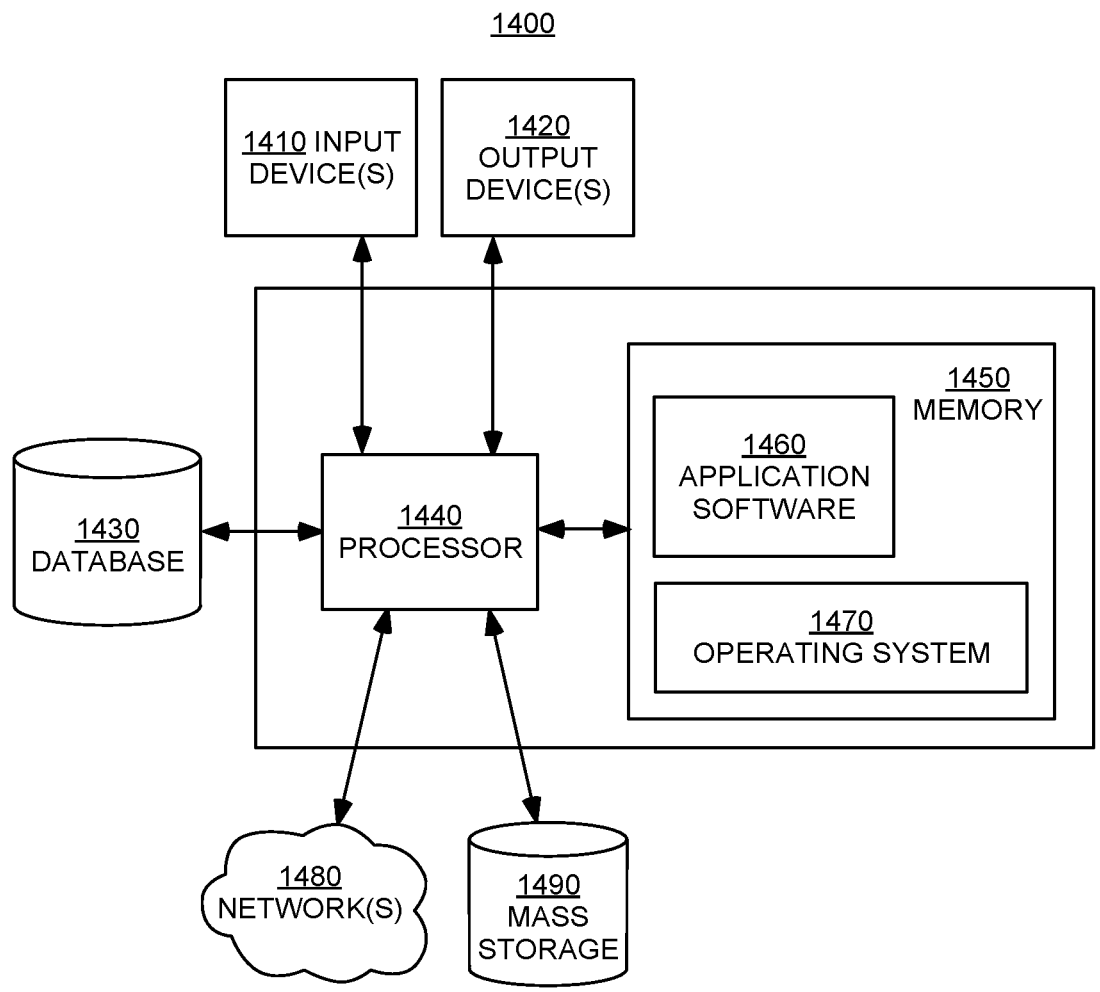
FIG. 14 shows a block diagram for an exemplary computer system for implementing customized sleep environment management systems as disclosed herein, according to one embodiment of the present invention.

FIG. 14 shows a block diagram for another exemplary computer system 1400 for implementing customized sleep environment management systems and methods as disclosed herein, according to some embodiments of the present invention. Computer system 1400 may be adapted for use as a sleep environment controller, or user device 140 in FIG. 1, or any other appropriate stand-alone or integrated modules and systems disclosed herein.

Computer system 1400 typically includes at least one processor 1440 that communicates with a number of peripheral devices via bus subsystem. Processor 1440 may be general purpose, or an ASIC or RISC processor. It may be an FPGA or other logic or gate array. It may include graphic processing unit (GPU) resources. Peripheral devices may include a storage subsystem including, for example, memory devices and a file storage subsystem, user interface input devices 1410, user interface output devices 1420, and a network interface subsystem 1480. The input and output devices allow user interaction with computer system 1400. Network interface subsystem 1480 provides an interface to outside networks, including an interface to corresponding interface devices in other computer systems.

User interface input devices 1410 may include a keyboard, pointing devices such as a mouse, trackball, touchpad, or graphics tablet, a scanner, a touch screen incorporated into the display, audio input devices such as voice recognition systems and microphones; and other types of input devices. In general, use of the term "input device" is intended to include the possible types of devices and ways to input information into computer system 1400.

User interface output devices 1420 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide a non-visual display such as audio output devices. In general, use of the term "output device" is intended to include the possible types of devices and ways to output information from computer system 1400 to the user or to another machine or computer system.

A storage subsystem stores programming and data constructs that provide the functionality of some or all of the modules and methods described herein. These software modules are generally executed by processor 1440 alone or in combination with other processors.

Memory 1450 used in the storage subsystem can include a number of memories including a main random-access memory (RAM) for storage of instructions and data during program execution and a read only memory (ROM) in which fixed instructions are stored. A file storage subsystem can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem in the storage subsystem, or in other machines accessible by the processor.

Computer system 1400 can be of varying types including a workstation, server, computing cluster, blade server, server farm, or any other data processing system or computing device. Due to the ever-changing nature of computers and networks, the description of computer system 1400 depicted in FIG. 14 is intended only as one example. Many other configurations of computer system 1400 are possible having more or fewer components than the computer system depicted in FIG. 14.

Figure 15:
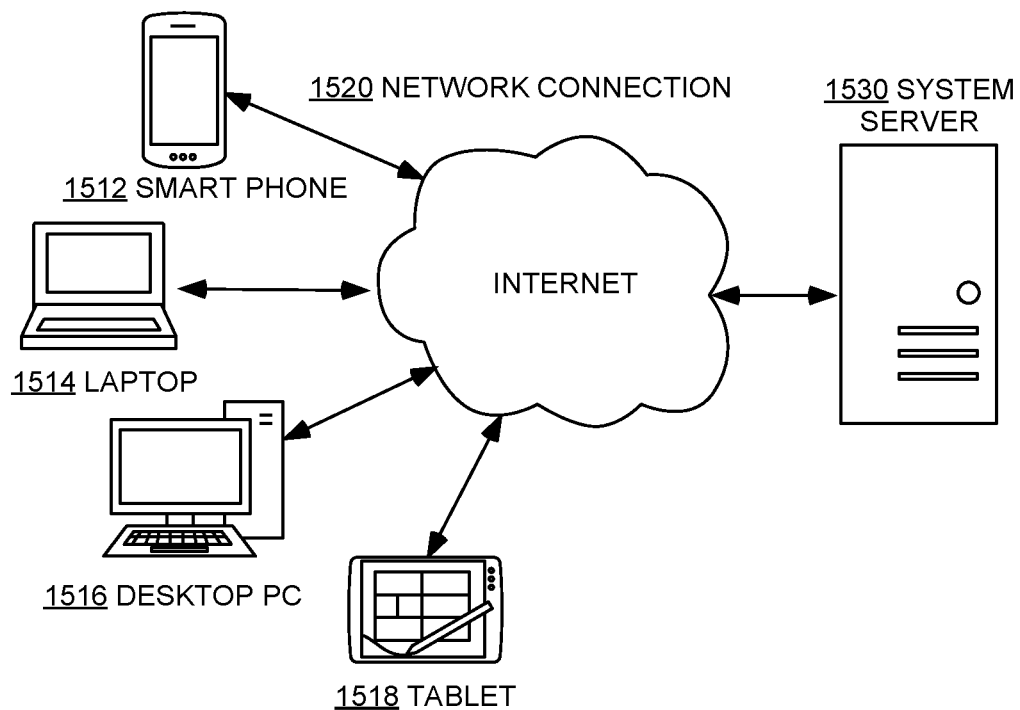
FIG. 15 shows an illustrative client-server architecture for implementing one embodiment of the present invention in a client server environment.

The present invention may be implemented in a client server environment. FIG. 15 shows an illustrative system architecture 1500 for implementing one embodiment of the present invention in a client server environment. User devices 1510 on the client side may include smart phones 1512, laptops 1514, desktop PCs 1516, tablets 1518, or other devices. Such user devices 1510 access the service of the system server 1530 through some network connection 1520, such as the Internet.

In some embodiments of the present invention, the entire system can be implemented and offered to the end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom software installation on the client side and increases the flexibility of delivery of the service (software-as-a-service), and increases user satisfaction and ease of use. Various business models, revenue models, and delivery mechanisms for the present invention are envisioned, and are all to be considered within the scope of the present invention.

Figure 16:
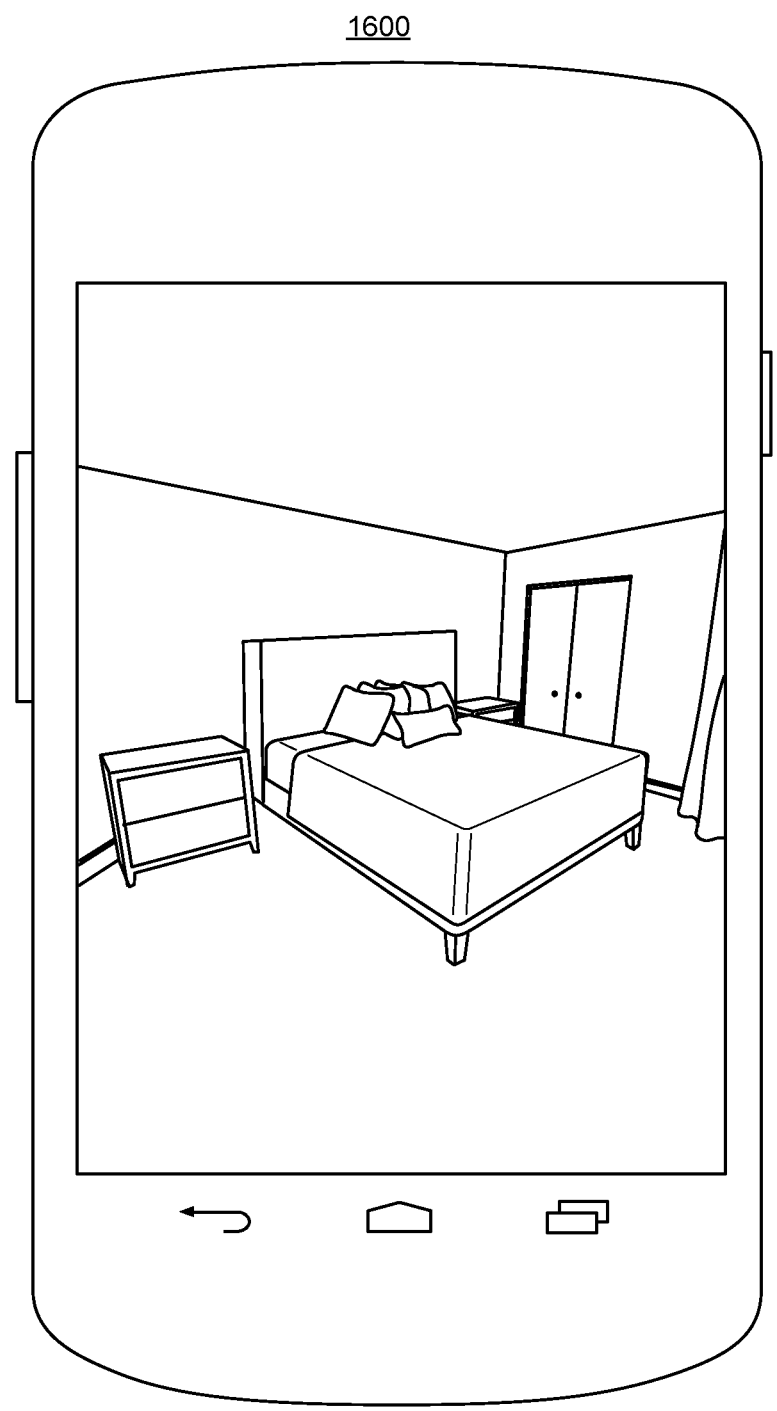
FIG. 16 shows an exemplary screenshot of a sleep environment controller's graphical user interface (GUI) on a mobile computing device, according to one embodiment of the present invention.
Figure 17:
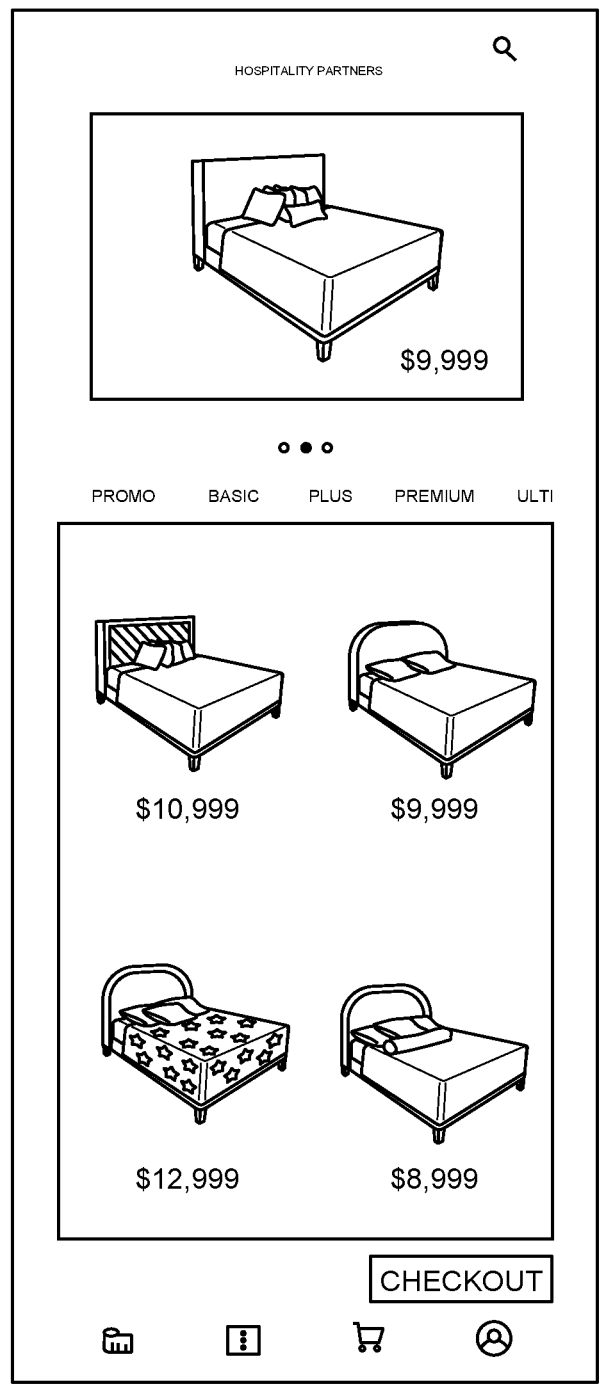
FIG. 17 shows an exemplary screenshot of a sleep environment controller's GUI for ordering custom sleep-related physical products from the sleep environment, according to one embodiment of the present invention.

In general, the method executed to implement the embodiments of the invention, may be implemented as part of an operating system or a specific application, component, program, object, module or sequence of instructions referred to as "computer program(s)" or "computer code(s)." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), and digital and analog communication media.
Sleep-Related Product Sales Through Sleep Environment Management System As disclosed herein, the sleep environment management system collects data on user behaviour and preferences, which in turn may be used to promote the sales of sleep-related products installed within the sleep environment itself. For example, FIG. 16 shows an exemplary screenshot 1600 of a sleep environment management graphical user interface (GUI) on a mobile computing device, which may allow a user to select individual objects within the sleep environment for control, monitoring, and/or purchase. FIG. 17 shows a corresponding exemplary screenshot 1700 of a mobile device GUI for ordering sleep-related products of interest, according to one embodiment of the present invention. In one embodiment, the user may click on an object shown in FIG. 16 to see available purchase options shown in FIG. 17. Though not explicitly shown in FIGS. 16-17, the user can browse sleep-related products of interest, view product information, control the sleep environment, order room service, order food service, order requests from the facility management system, submit requests for transportation or concierge services, change or update their hotel reservations, find local points of interest, order taxis or car service, and perform a variety of other useful functions, all from the same GUI on the user device.

FIG. 18 shows a schematic of an exemplary sell-through method 1800, according to one embodiment of the present invention. The sell-through method may comprise four steps. In an installation step 1810, custom sleep-related products are provided by a sleep environment company to hospitality partners. In a guest experiences step 1820, guests enjoy the sleep-related products in a managed sleep environment in a first-hand experience, where their appreciation of the sleep-related products may be heightened by subtle touch-point communications. In a sell-through step 1830, guests purchase sleep-related products for home directly from a company-managed custom sleep environment branded web portal. In an earnings step 1840, sell-through earnings may be divided between the hospitality partners and the sleep environment company.

Figure 19:
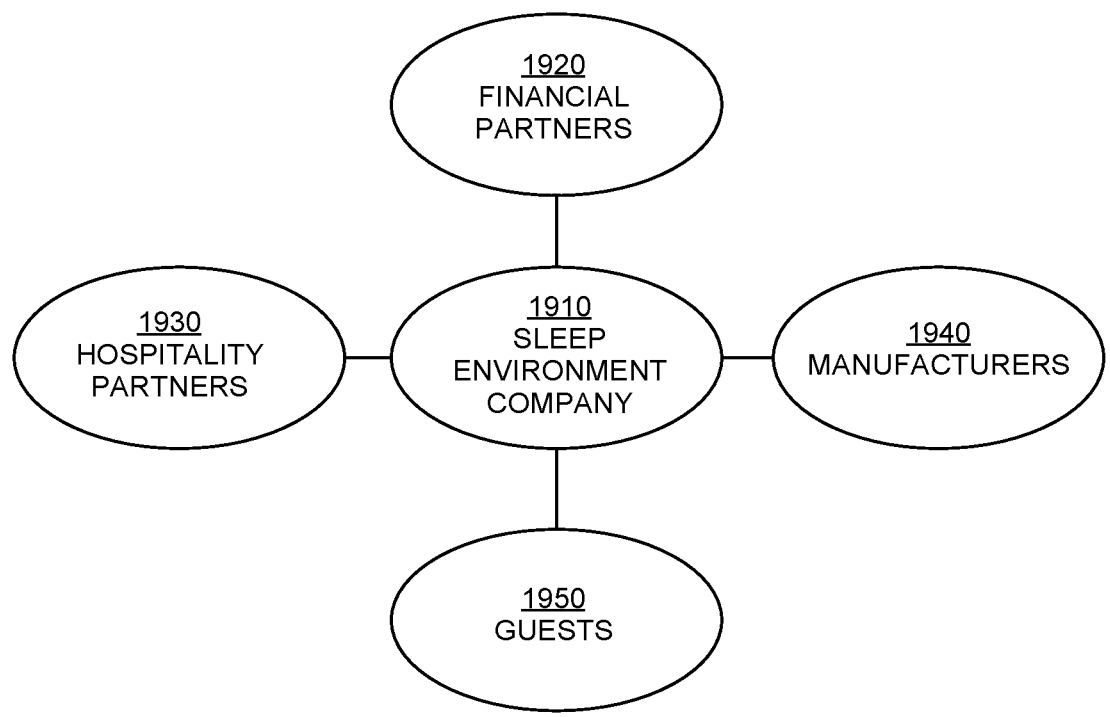
FIG. 19 shows a schematic of a relationship between various organizational entities involved in using the present invention, according to one embodiment of the present invention.

FIG. 19 shows a schematic 1900 of a relationship between various organizational entities involved in the sell-through process, where a sleep environment company 1910 may interact with financial partners 1920 who provide funding for the upgrades to the hospitality partner venues, hospitality partners 1930 who provide the hospitality and sleep environments, sleep-related product manufacturers 1940 who supply the sleep-related products, and hospitality guests 1950 who experience the sleep environment and purchase products of interest.

The installation of the sleep environments with the hospitality partners 1930 generates revenues for the sleep environment company 1910 and the other stakeholders in three ways: 1) increased room rates; 2) increased wholesale operating margins; and 3) sell-through, as guests purchase the systems, or elements thereof, for their homes.

The model creates winning propositions for all parties involved: the financial partners 1920, the hospitality partners 1930, the manufacturers 1940, the hospitality guests 1950, and the sleep environment company 1910. Financial partners 1920 see higher than normal returns for their investments which are backed by the assets productively placed into service and contracts with recognized luxury brands. Hospitality partners 1930 get the benefit of state-of-the-art sleep technology at no cost, which creates greater guest satisfaction, market differentiation, drives higher room rates and creates a previously unrealized profit-center, increasing EBITDA from shared "sell-through" revenues. The manufacturing partners and other suppliers 1940 receive significant sales increases on both initial installations to the properties and sell-through sales. Guests 1950 experience the absolute best sleep system in the world, and enhanced-health room environment, with a chance to bring the technology to their own homes. The sleep environment company 1910, in turn, benefits handsomely from the enhancement it has brought to all of these relationships.

Sleep Environment Management Method

Figure 20:
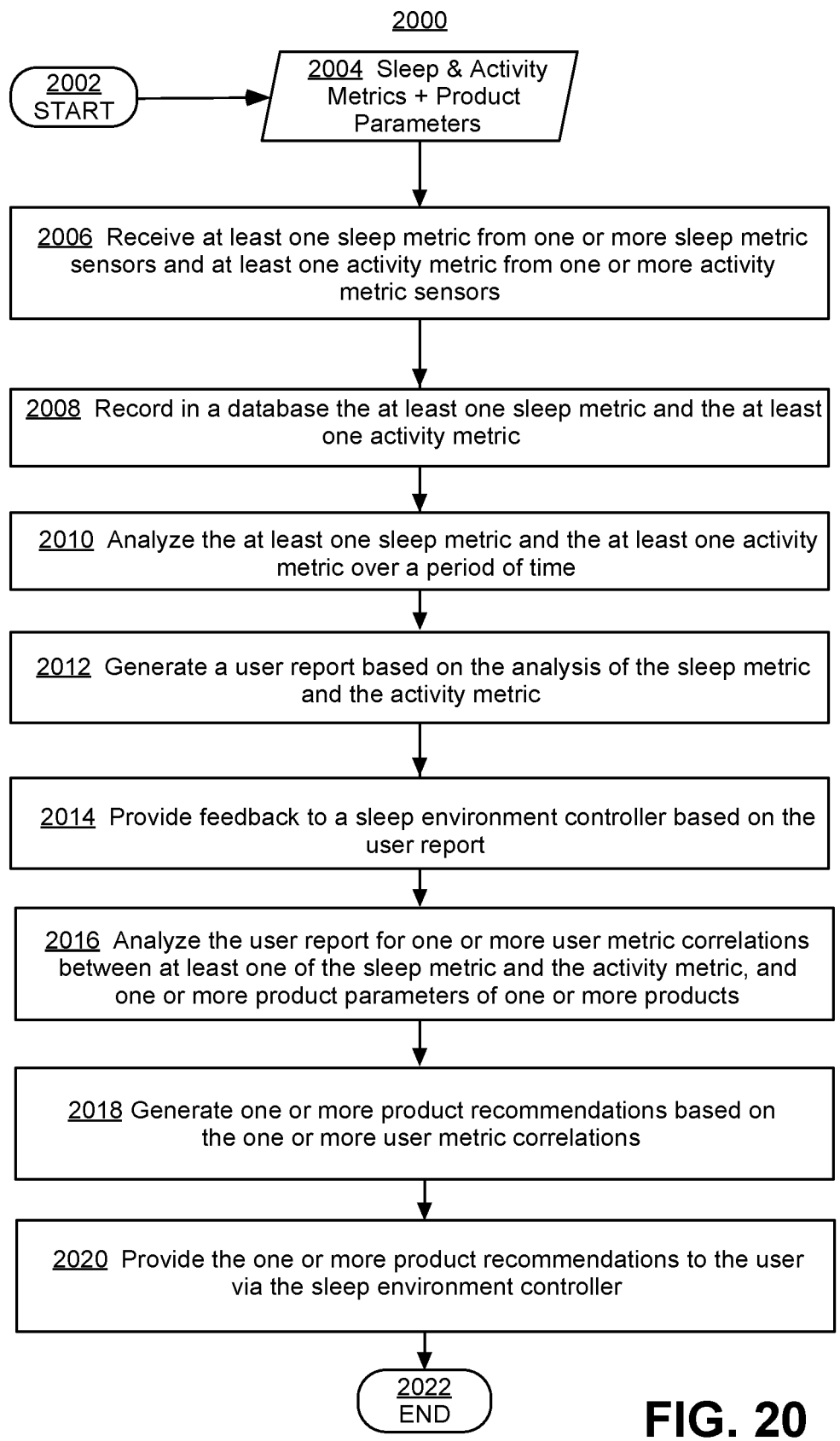
FIG. 20 shows an exemplary flow chart of an exemplary method for sleep environment management, according to one embodiment of the present invention.

FIG. 20 shows an exemplary flow chart 2000 of an exemplary method, according to one embodiment of the present invention. A method for sleep environment management and product recommendations via a hospitality environment starts at step 2002. The inputs to the method comprise data from sleep and activity metric sensors and product parameters 2004.

At step 2006, the method receives from a sleep environment, over a period of time, at least one sleep metric of a user from one or more sleep metric sensors for detecting sleep quality of the user, and at least one activity metric of the user from one or more activity metric sensors for human activity recognition within a sleep space, wherein the human activity comprises lying on a bed, sitting, and/or walking in the sleep environment.

At step 2008, the method records in the database the at least one sleep metric and the at least one activity metric.

At step 2010, the method analyses the at least one sleep metric and the at least one activity metric over the period of time.

At step 2012, the method generates a user report based on the analysis of the sleep metric and the activity metric.

At step 2014, the method provides feedback to the sleep environment controller based on the user report.

At step 2016, the method analyzes the user report for one or more user metric correlations between at least one of the sleep metric and the activity metric, and one or more product parameters of one or more physical products in the sleep environment. In one embodiment, a machine learning (ML) module, for example, a random forest algorithm as shown in FIG. 10B, is utilized to calculate the correlations.

At step 2018, the method generates one or more product recommendations based on the one or more user metric correlations, wherein the one or more product recommendations comprise at least one physical product from the sleep environment.

At step 2020, the method provides the one or more product recommendations to the user via the sleep environment controller. The method ends at step 2022.

Illustrative Advantages of the Present Invention

Figure 21:
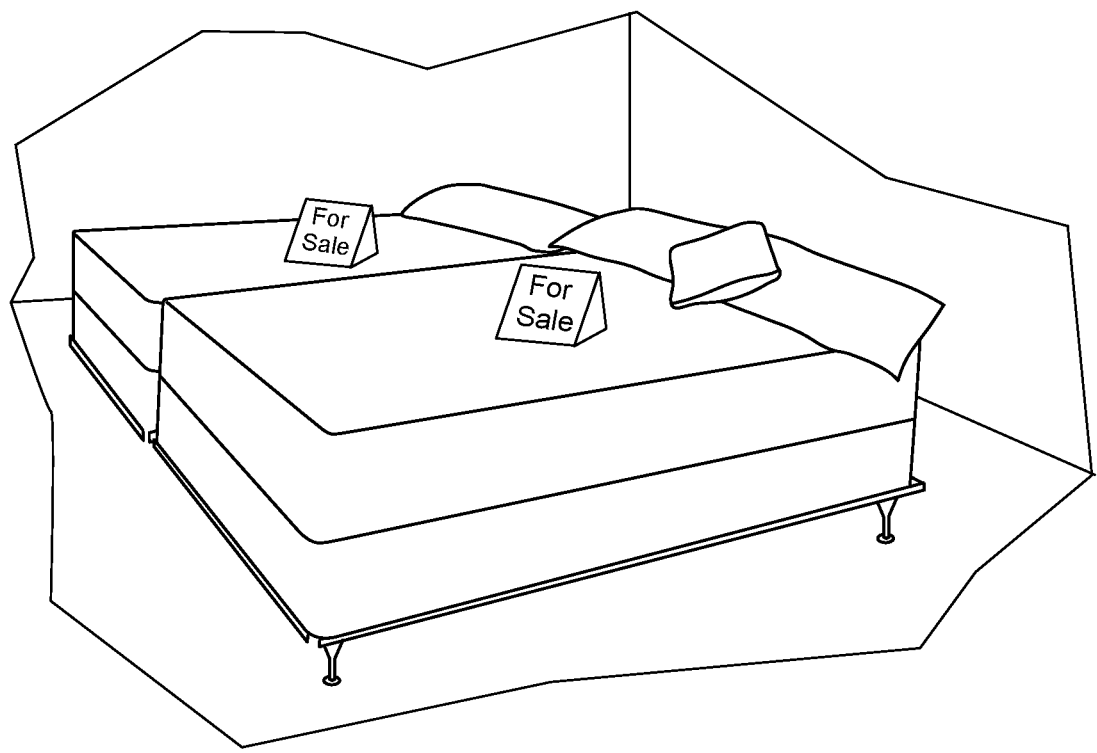
FIG. 21 shows a prior art showroom environment in a traditional retail environment.

The system of the present invention is in sharp contrast to the dry look and feel of traditional sleep product sales environment, such as a bed and mattress show room, as shown in FIG. 21. Several illustrative advantages of the sleep environment management system as disclosed by the present invention are now described. These advantages are not to be read as limiting the scope of the present invention.

Overall Advantages: (1) Ability of bundling the sleep system or bed, with a sound system and other sleep-related products; (2) Guest can shop for items inside the hotel room using a portal to order right from the room and can order individual components or the entire system; (3) Mobile device controls the room, temperature, heat, concierge, understands what the sleep system does, what the hydroxyl generator is about, etc.; (4) Server in the cloud, communicates with the customer, gathers information, provides selling opportunity; and (5) Hotel credit system, in which the hotel acts as a sales channel, eliminates salespeople, overhead, etc.

Hospitality Guest Advantages: (1) Receives the most technologically-advanced sleep experience in the world; (2) Experiences better quality, rejuvenating sleep, enhancing their vacation experience; (3) Can seamlessly recreate this luxury and health-affirming experience in their home; (4) Feels perceptible "wow" factor from the bed/room environment; and (5) Opportunity to test-run before purchase.

Hospitality Venue Advantages: (1) Gives their guests a comprehensive luxury, health experience which produces a unique "wow" factor; (2) Increases their financial performance; (3) Obtains a greatly improved sleep system, the most important consideration of a guest, with no capital investment required; (4) Achieves increased brand differentiation and increased loyalty by offering unique and superior sleep environment; and (5) Is able to market their hotel as offering the best sleep environment in world and an allergy-friendly, virus/mold/bacteria free room.

One of ordinary skill in the art knows that the use cases, structures, schematics, and flow diagrams may be performed in other orders or combinations, but the inventive concept of the present invention remains without departing from the broader scope of the invention. Every embodiment may be unique, and methods/steps may be either shortened or lengthened, overlapped with other activities, postponed, delayed, and continued after a time gap, such that every user is accommodated to practice the methods of the present invention.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention as defined by the appended claims.

What is claimed is:

1. A system for sleep environment management and product recommendations via a hospitality environment, comprising:
　　a sleep environment located in the hospitality environment, comprising:
　　　　a bed located inside a walled sleep space;
　　　　one or more sleep metric sensors for detecting sleep quality of a user;
　　　　one or more activity metric sensors for human activity recognition within the walled sleep space, wherein the human activity comprises lying on the bed, sitting, and/or walking in the sleep environment; and
　　　　a sleep environment controller; and
　　a server comprising a hardware processor, the server having access to a database, and the server comprising a non-transitory, computer-readable storage medium for storing program code, the program code programmed to be executed by the processor, the processor configured to:
　　　　receive from the sleep environment, over a period of time, a sleep metric of the user from the sleep metric sensors and an activity metric of the user from the activity metric sensors;
　　　　record in the database the sleep metric and the activity metric;
　　　　analyze the sleep metric and the activity metric over the period of time;
　　　　generate a user report based on the analysis of the sleep metric and the activity metric;

provide feedback to the sleep environment controller based on the user report;

analyze via machine learning algorithms, the user report for one or more user metric correlations between at least one of the sleep metric and the activity metric, and one or more product parameters of one or more sleep-related physical products in the sleep environment;

generate one or more sleep-related product recommendations based on the one or more user metric correlations, wherein the one or more sleep-related product recommendations comprise at least one sleep-related physical product among the one or more sleep-related physical products in the sleep environment; and provide the one or more product recommendations to the user via the sleep environment controller.

2. The system of claim 1, wherein the sleep environment further comprises an air purification unit selected from the group consisting of a hydroxyl generator, a photocatalytic oxidation (PCO) system, an ozone generator, and an ultraviolet (UV) light system.

3. The system of claim 1, further comprising a user device comprising a user interface, and program code to:

establish a communication channel between the user interface on the user device and the server, wherein the user interface is used by a plurality of stakeholders to access the processor for providing the one or more product parameters of the one or more sleep-related physical products from the sleep environment, and wherein the server houses the plurality of product parameters of the sleep-related products.

4. The system of claim 1, further comprising program code to:

receive input from the user from a universal remote in the sleep environment; and present information to educate the user with features of the one or more sleep-related physical products presented in the sleep environment on the universal remote.

5. The system of claim 1, further comprising program code to:

correlate the sleep metric and the activity metric from the user across time to predict expected behaviors of the user based on analysis of prior behaviors of the user in similar conditions.

6. The system of claim 1, further comprising program code to:

correlate the sleep metric and the activity metric from two or more users across time to predict expected behaviors of the user based on analysis of prior behaviors of other users in similar conditions.

7. The system of claim 6, further comprising program code to:

provide machine learning algorithm based recommendations on the one or more sleep-related physical products for the user based on the correlation of the sleep metric and the activity metric from the two or more users across time.

8. The system of claim 1, further comprising program code to:

provide the user report, subject to user permission, to a hospitality partner for improving the user's hospitality experience.

9. The system of claim 1, further comprising program code to:

provide the user report, subject to user permission, to a hospitality products company for generating customized sleep recommendations and/or product information.

10. The system of claim 1, wherein the sleep environment controller adjusts the sleep environment based on the feedback.

11. The system of claim 10, wherein the user report identifies a minimum time the user spends in various locations within the sleep environment, and further comprising program code to:

receive data from a sleep sensor in the sleep environment, wherein the data indicates a minimum depression and the minimum time the user spends in the sleep environment.

12. The system of claim 11, further comprising an actuator for controlling objects within the sleep environment, and further comprising program code to:

move physical objects within the sleep environment in response to the user's location.

13. The system of claim 11, further comprising program code to:

modify a scent and an air quality within the sleep environment in response to the user's location.

14. The system of claim 10, further comprising program code to:

detect a location of the user in the sleep environment and continuously record an array of coordinates of the user's location in the user report.

15. The system of claim 1, wherein the user report identifies a location of the user in the sleep environment.

16. The system of claim 1, further comprising program code to:

retrieve stored sleep metrics and activity metrics from the database to generate a population report; and adjust the sleep environment in response to feedback based on the population report.

17. The system of claim 1, further comprising program code to:

receive user-specific feedback from the user; and correlate the user-specific feedback using a series of pre-defined weights and tolerances to collect, interpret, and analyze sleep habits associated with the user.

18. The system of claim 1, further comprising:

an environmental digital logic module integrated into the sleep environment, wherein the environmental digital logic module controls one or more environmental conditions within the sleep environment, the environmental conditions comprising one of temperature and humidity, wherein the environmental digital logic module provides the environmental conditions of the sleep environment to the server for storage in the database along with the sleep metric and the activity metric.

19. The system of claim 1, wherein the sleep metric sensor is selected from the group consisting of a heart rate sensor, an oximeter, a pressure sensor, and a roll-over detector, wherein the activity metric sensor is selected from the group consisting of a motion sensor and a pressure sensor, and wherein the sleep environment further comprises one of a temperature sensor, a humidity sensor, and an air quality monitor.

20. A method for managing a sleep environment and product recommendations via a hospitality environment, the sleep environment located in the hospitality environment, the sleep environment comprising a bed located inside a walled sleep space, one or more sleep metric sensors for detecting sleep quality of a user, one or more activity metric sensors for human activity recognition within the walled sleep space, and a sleep environment controller, the method comprising:

receiving from the sleep environment located within the hospitality environment, over a period of time, a sleep metric of the user from the sleep metric sensors and an activity metric of the user from the activity metric sensors;

recording in a database the sleep metric and the activity metric;

analyzing the sleep metric and the activity metric over the period of time;

generating a user report based on the analysis of the sleep metric and the activity metric;

providing feedback to the sleep environment controller based on the user report;

analyzing via machine learning algorithms, the user report for one or more user metric correlations between at least one of the sleep metric and the activity metric, and one or more product parameters of one or more sleep-related physical products in the sleep environment;

generating one or more sleep-related product recommendations based on the one or more user metric correlations, wherein the one or more sleep-related product recommendations comprise at least one sleep-related physical product among the one or more sleep-related physical products in the sleep environment; and providing the one or more product recommendations to the user via the sleep environment controller.

21. A non-transitory storage medium storing executable program code, the program code configured to execute a process for managing a sleep environment and product recommendations via a hospitality environment, the program code configured to:

receive from the sleep environment located within the hospitality environment, over a period of time, a sleep metric of the user from one or more sleep metric sensors and an activity metric of the user from one or more activity metric sensors, wherein the sleep environment comprises a bed located inside a walled sleep space;

record in a database the sleep metric and the activity metric;

analyze the sleep metric and the activity metric over the period of time;

generate a user report based on the analysis of the sleep metric and the activity metric;

provide feedback to a sleep environment controller based on the user report;

analyze via machine learning algorithms, the user report for one or more user metric correlations between at least one of the sleep metric and the activity metric, and one or more product parameters of one or more sleep-related physical products in the sleep environment;

generate one or more sleep-related product recommendations based on the one or more user metric correlations, wherein the one or more sleep-related product recommendations comprise at least one sleep-related physical product among the one or more sleep-related physical products in the sleep environment; and provide the one or more product recommendations to the user via the sleep environment controller.

* * * * *